United States Patent
Phillips et al.

(10) Patent No.: US 7,043,402 B2
(45) Date of Patent: May 9, 2006

(54) ON-LINE OIL CONDITION SENSOR SYSTEM FOR ROTATING AND RECIPROCATING MACHINERY

(75) Inventors: Alan D. Phillips, Trenton, NJ (US); William J. Eggers, Knoxville, TN (US); Robert S. Rodgers, Hightstown, NJ (US); Dean Pappas, Hamilton Square, NJ (US)

(73) Assignee: The Precision Instrument Corp., Trenton, NJ (US)

( * ) Notice: Subject to any disclaimer, the term of this patent is extended or adjusted under 35 U.S.C. 154(b) by 18 days.

(21) Appl. No.: 10/323,082

(22) Filed: Dec. 19, 2002

(65) Prior Publication Data

US 2003/0222656 A1 Dec. 4, 2003

Related U.S. Application Data

(60) Provisional application No. 60/342,686, filed on Dec. 20, 2001.

(51) Int. Cl.
 *G01R 27/00* (2006.01)
(52) U.S. Cl. .......................... 702/184; 702/50; 702/64; 702/65; 324/605; 324/600
(58) Field of Classification Search ................ 702/184, 702/183, 25, 50, 22, 30–32, 57, 64, 65, 72, 702/75, 81, 114, 130, 132, 136, 137, 99, 100, 702/106, 189; 324/71.1, 698, 663, 664, 667, 324/690, 691, 694, 553, 600, 640, 675, 684, 324/605, 707; 73/53.05, 53.01, 53.06, 54.01, 73/54.02, 53.07, 116, 304 R, 117.3; 340/603, 340/631, 457.4; 701/30
See application file for complete search history.

(56) References Cited

U.S. PATENT DOCUMENTS

| 4,646,070 A | 2/1987 | Yasuhara et al. ........... 340/603 |
| 4,701,713 A | 10/1987 | Eaton et al. ................ 324/442 |
| 4,719,441 A | 1/1988 | Horn ........................... 338/20 |
| 4,733,556 A | 3/1988 | Meitzler et al. ........... 73/53.05 |
| 4,742,476 A | 5/1988 | Schwartz et al. ............. 701/30 |

(Continued)

OTHER PUBLICATIONS

On-Line System for Lubrication Diagnostics by Heiner Kaden, Wolfgang Fichtner and Kristina Ahlborn; MTZ Worldwide; pp. 8-11, no date.

(Continued)

*Primary Examiner*—Hal Wachsman
(74) *Attorney, Agent, or Firm*—Reed Smith LLP

(57) ABSTRACT

An on-line sensing system and method for monitoring in real-time thermal-oxidative breakdown, water contamination, and/or fuel dilution conditions in operational engine lubricating oils. The method of the invention includes an electrochemical impedance analysis technique specific to the particular oil to be monitored. Sensing devices having of at least two electrodes are configured for direct installation in an existing access port, or drain port, of a lubricating oil reservoir. An AC voltage waveform is applied to the sensing device (preferably less than 100 Hz) to produce voltage and current responses between the appropriate electrodes contacting the oil. The magnitude impedance |Z| and phase angle components of the complex impedance are used to characterize the quality and/or condition of the engine oil under test. The system also provides an electrical indication indicative of the percentage remaining useful life of the oil.

40 Claims, 24 Drawing Sheets

U.S. PATENT DOCUMENTS

| | | | | |
|---|---|---|---|---|
| 4,847,768 | A | | 7/1989 | Schwartz et al. ............. 701/30 |
| 5,071,527 | A | | 12/1991 | Kauffman ................... 205/786 |
| 5,200,027 | A | | 4/1993 | Lee et al. ...................... 216/51 |
| 5,274,335 | A | | 12/1993 | Wang et al. ................ 324/689 |
| 5,540,086 | A | | 7/1996 | Park et al. ................. 73/53.05 |
| 6,028,433 | A | * | 2/2000 | Cheiky-Zelina et al. .... 324/663 |
| 6,255,954 | B1 | * | 7/2001 | Brown et al. ............... 340/603 |
| 6,268,737 | B1 | * | 7/2001 | Marszalek .................. 324/663 |
| 6,377,052 | B1 | * | 4/2002 | McGinnis et al. .......... 324/446 |
| 6,459,995 | B1 | * | 10/2002 | Collister ...................... 702/23 |
| 6,577,112 | B1 | * | 6/2003 | Lvovich et al. ............ 324/71.1 |

OTHER PUBLICATIONS

In-situ Oil Condition Monitoring in Passenger Cars; Lee, Wang, and Smolenski; Lubrication Engineering 50, 8, 605-611, Nov. 1993.

In-Situ Monitoring of High Temperature Degraded Engine Oil Condition w/ Microsensors; Lee, Wang, and Smolenski; Sensor and Actuators B 20 (1994) 49-54, no month.

An Electrochemical Technique for Characterizing Metal-Lubricant Interfacial Reactions; Wang, Maheswari, and Tung; ASLE Transactions 30, 3, 394-402, no date.

AC Impedance Measurements of the Resistance and Capacitance of Lubricants; Wang, Maheswari, and Tung; ASLE Transactions 30, 4, pp. 436-439, 441-443, no date.

Using Electrochemical and Spectroscopic Techniques as Probes for Investigating Metal-Lubricant Interactions; Wang and Tung; Tribology Transactions 33 (1990), 4, 563-572.

A Sensor for Glycol C ntamination in Oil; Wang and Lee; Proc. of Journal of Electroch mical Soci ty, Abstract 692 (1992), 995-996.

Electr chemical Monitoring f Water-Surfactant Interactions in Industrial Lubricants; Lvovich, V.F.; J. Electroanalytical Society, 534 (2002) 171-180, no month.

Electrical Conductivity Method for Evaluation of Oxidative Degradation of Oil Lubricants; Sato, A. and Oshika, T.; Lubrication Engineering 48 (1991) 539-544.

Additives—The Right Stuff for Automotive Engin Oils; Watson and McDonnell, Jr.; SAE Paper No. 841208, pp. 17-28, Amoco Chemicals Corporation, Naperville, IL, no date.

Change in Performanc of Engine Oils with D gradation; In ue and Yamanaka; SAE Paper No. 902122, pp. 1-10 (1990), Nippon Oil Company, Ltd.

Experimental and Modeling Study of Kinetics and Selectivity in the Oxidation of a PAO Lubricant; Koh, C-S and Butt, J B.; Industrial Engineering Chemistry Research, vol. 34, No. 2, pp. 524-535, 1995, no month.

Water in Oil Analysis for Condition Monitoing; W. J. Leszek; Senior Research Fellow, IM Politechnika Paznanska, 60, 965, pp. 444-447, Poznan, Poland.

* cited by examiner

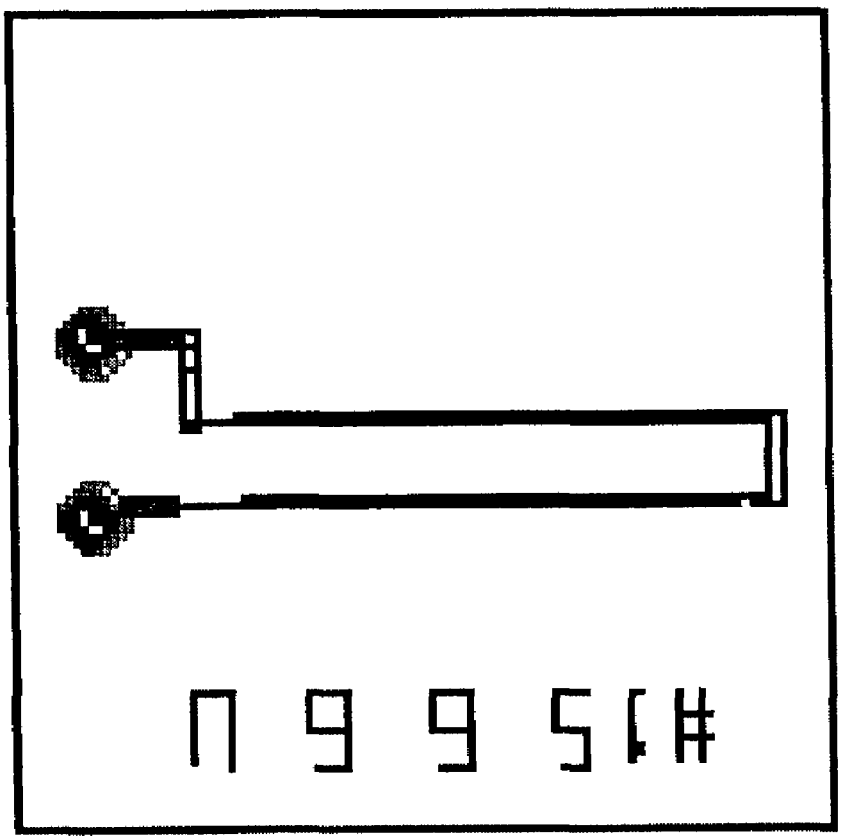
FIG. 1 – Parallel Planar-type Sensor Device

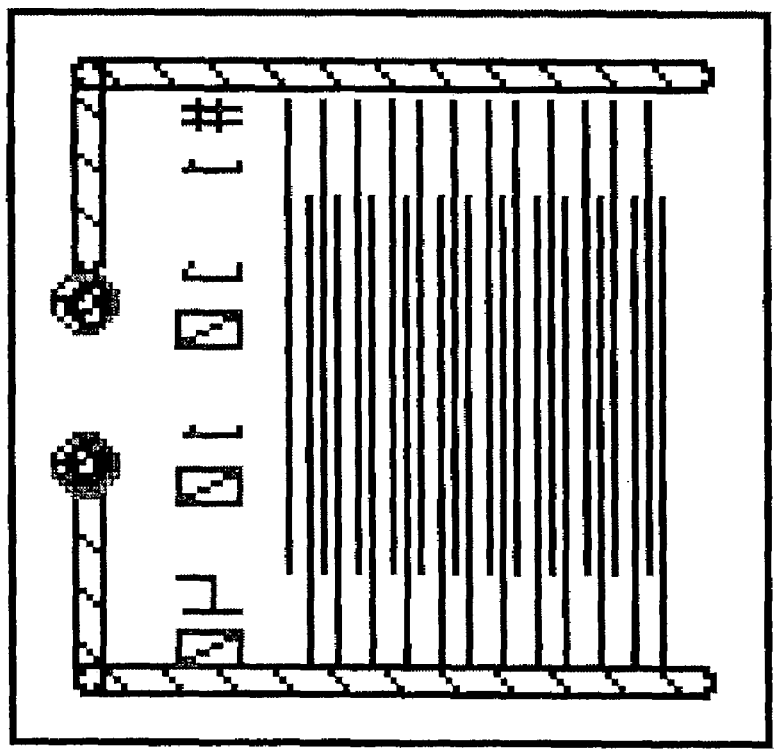
FIG. 2 – Interdigitated Planar-type Sensor Device

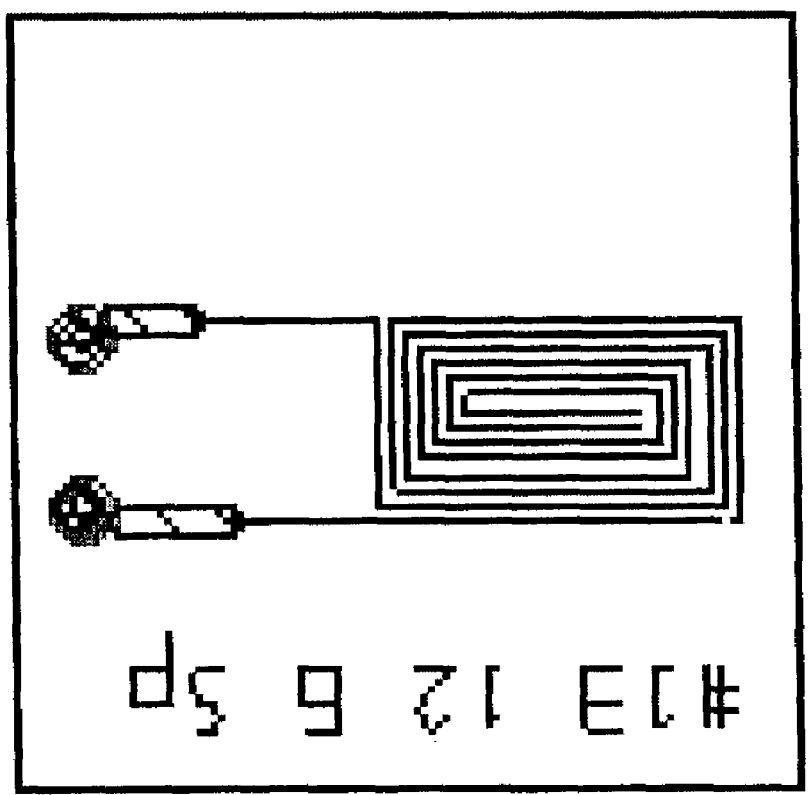
FIG. 3 – Concentric Planar-type Sensor Device

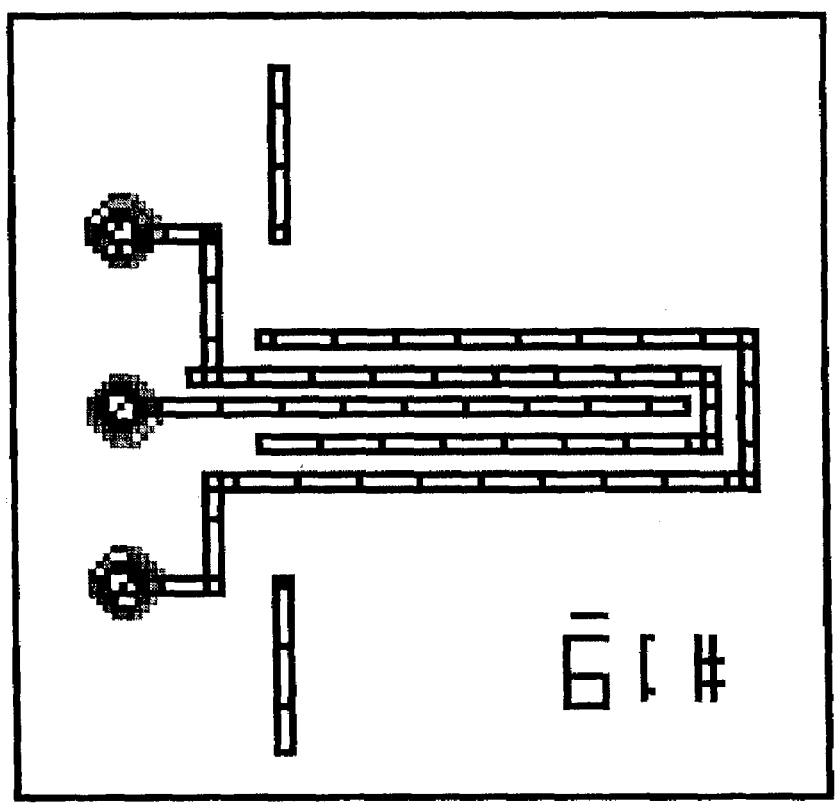
FIG. 4 – Planar-type, Three-electrode Sensor Device

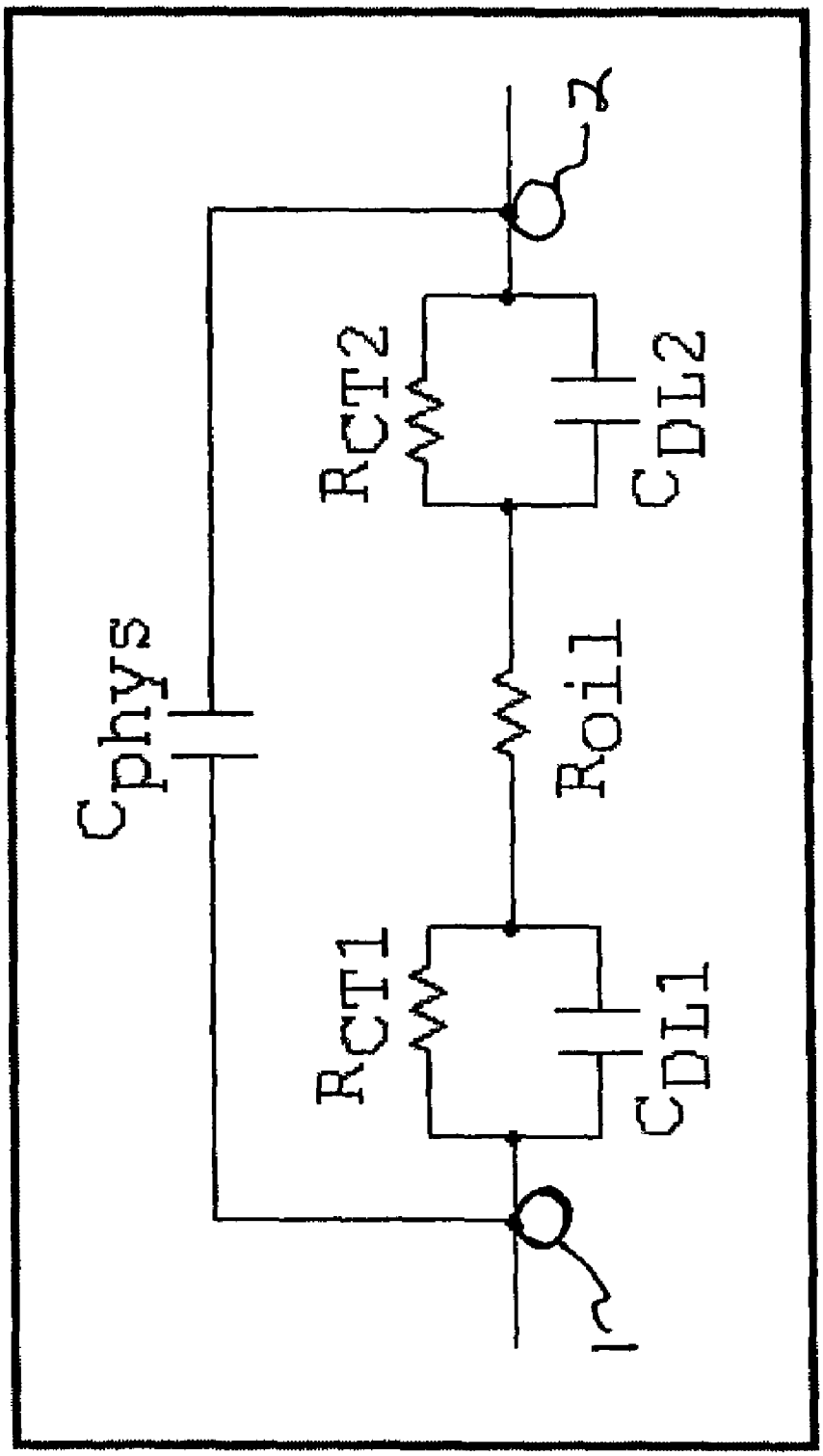
FIG. 5 – Sensor Equivalent Circuit

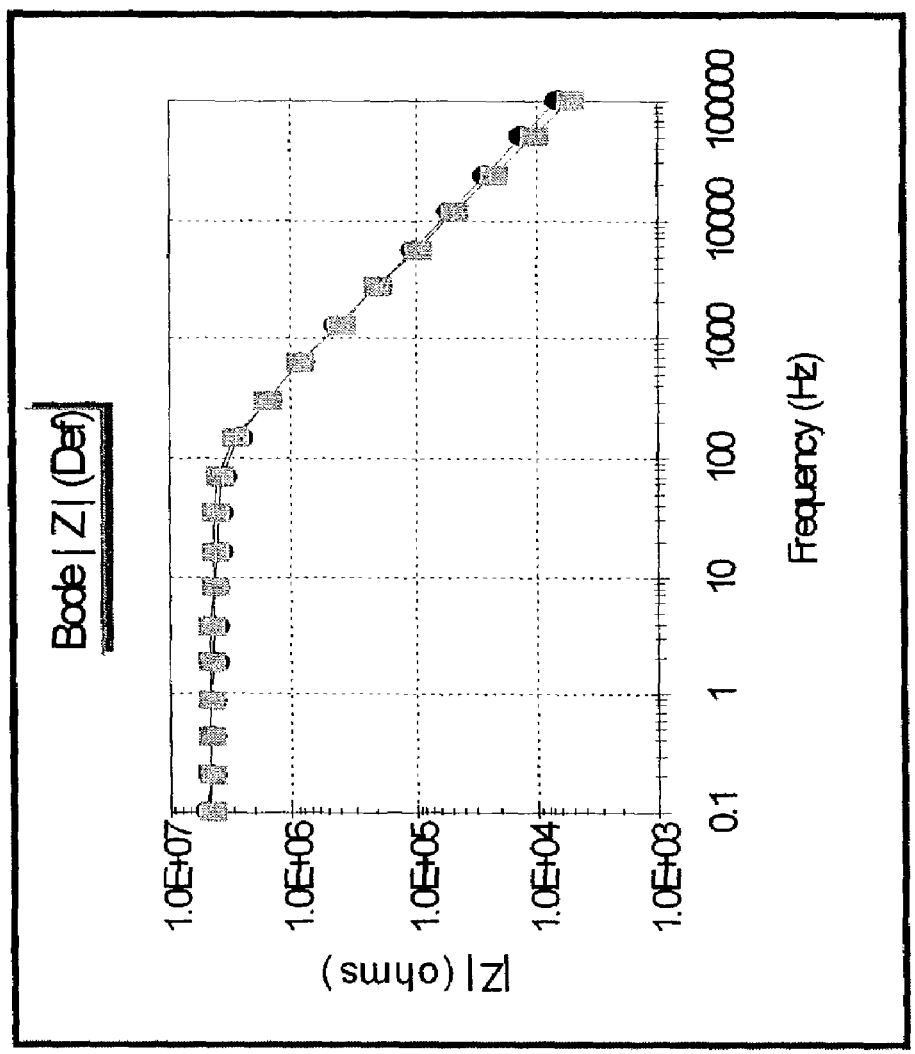
FIG. 6 – A Bode "Z" Plot Defined

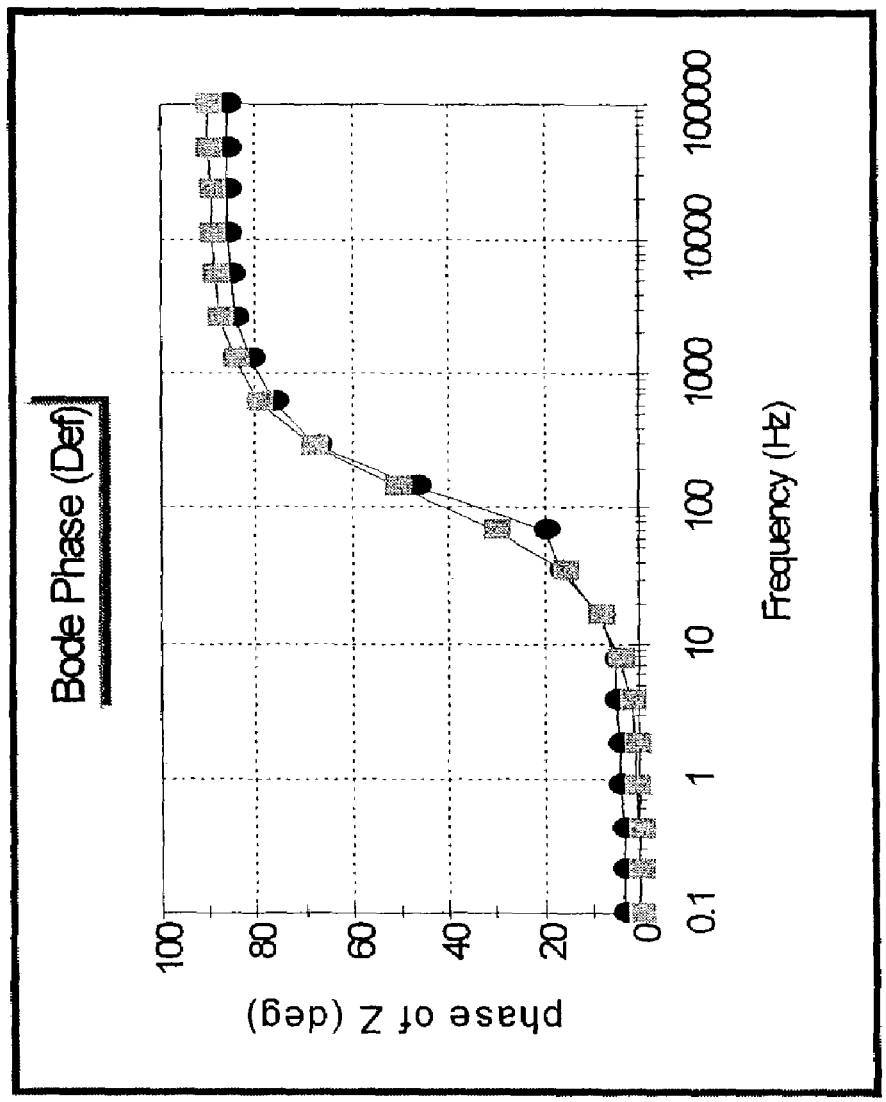
FIG. 7 – A Bode Phase Plot Defined

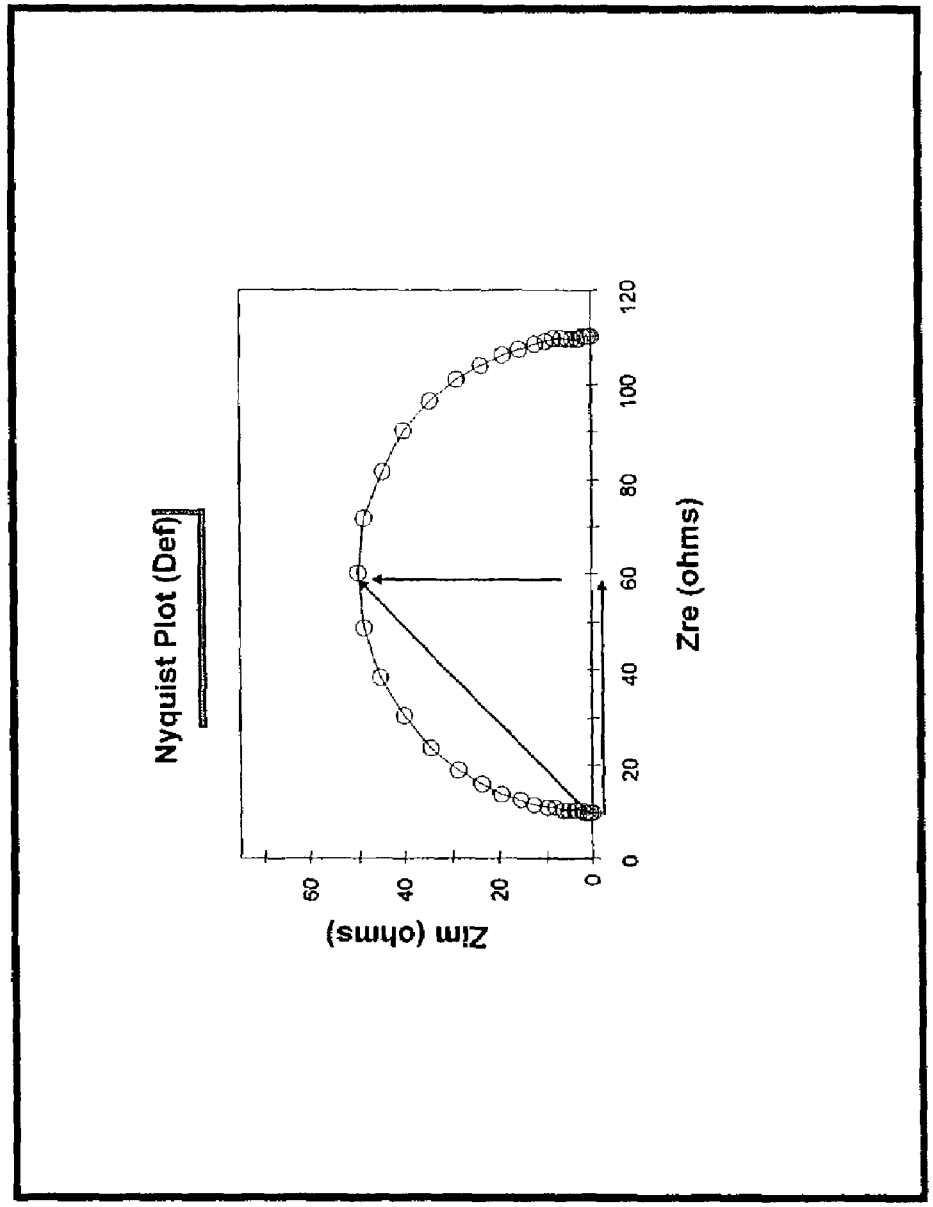
FIG. 8 – Classic Nyquist Plot Defined

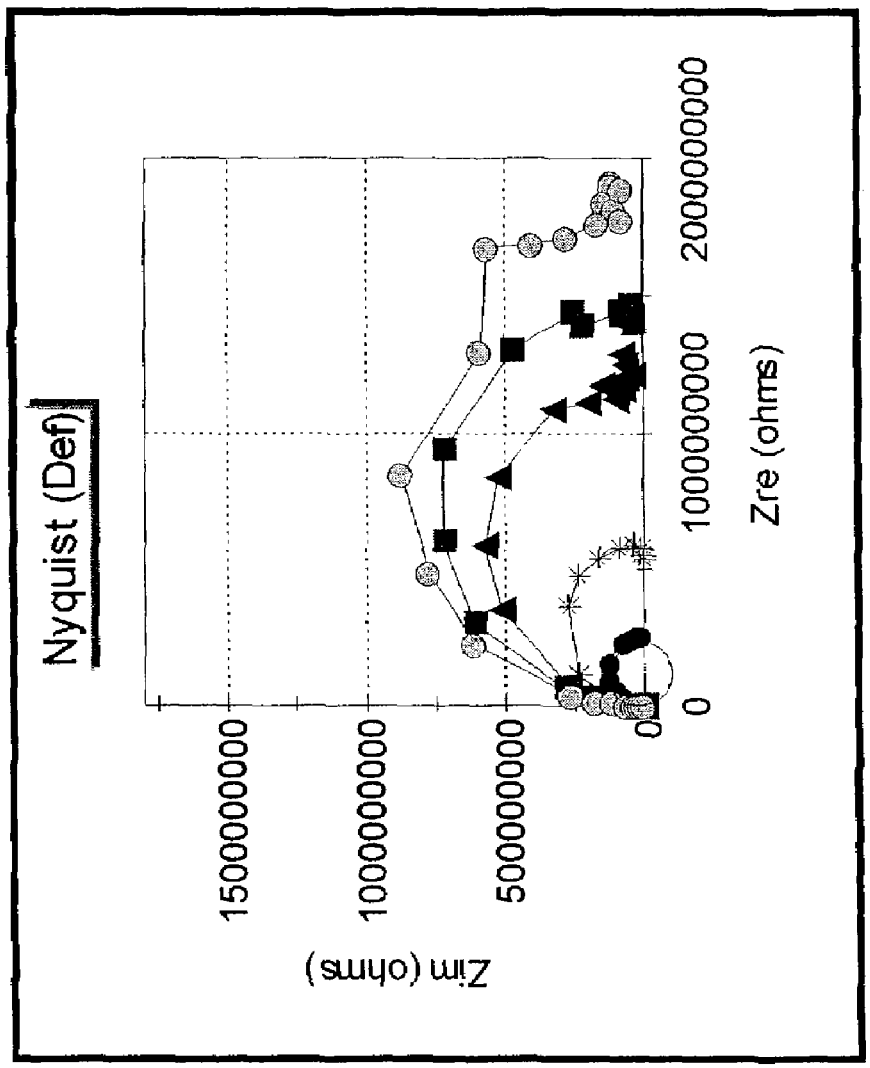
FIG. 9 – Nyquist Plots for Fresh and Degraded Oils

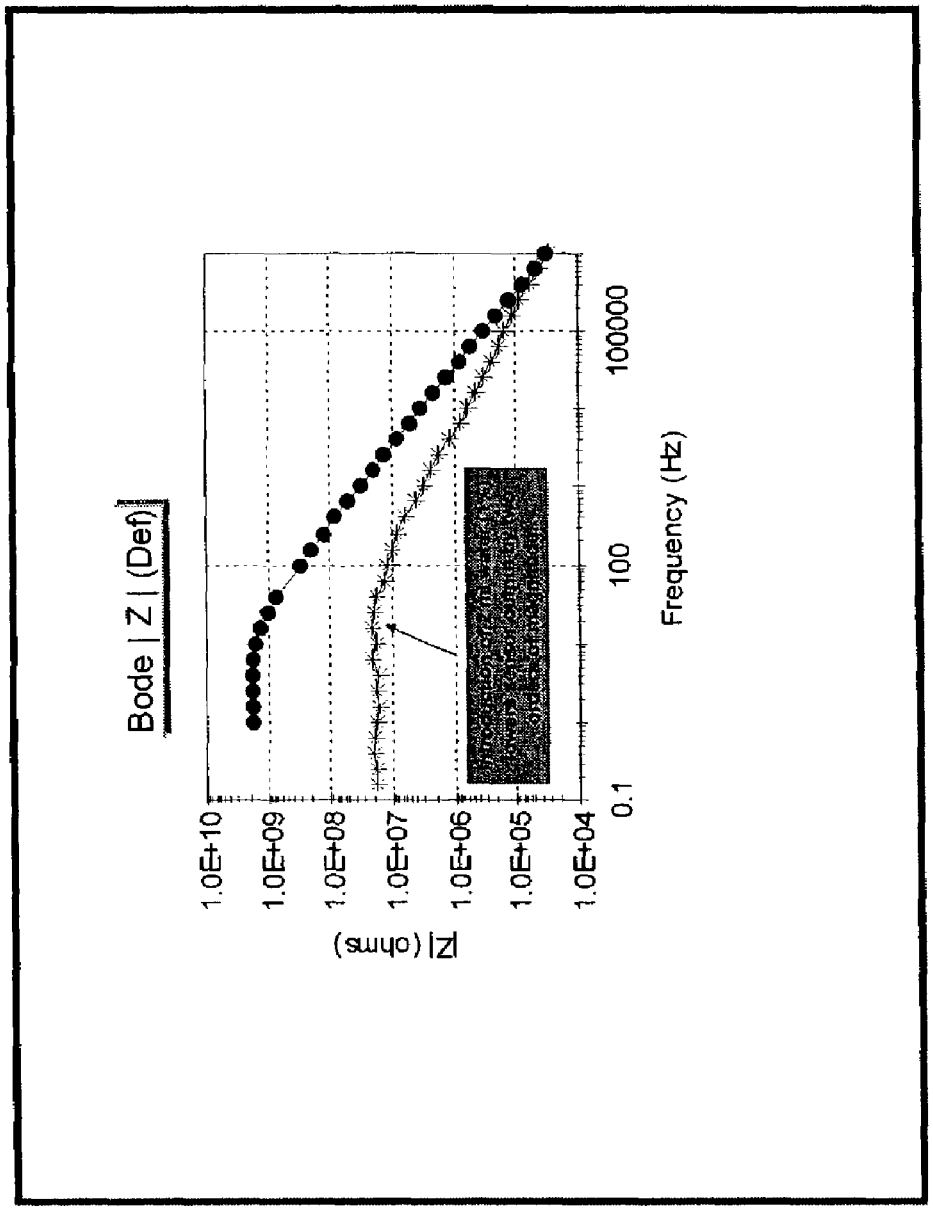
FIG. 10 – Bode Plot for Water Contamination

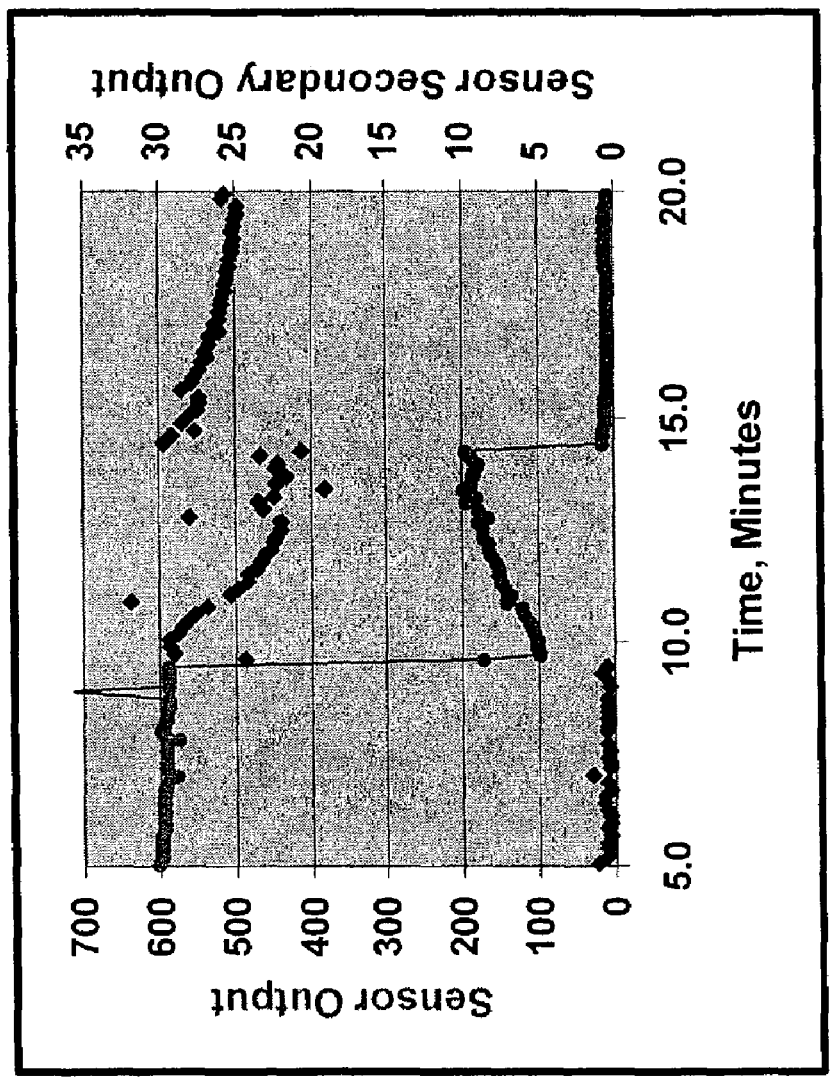
FIG. 11 – Magnitude Impedance „Z„ and Phase as a Function of Water Contamination

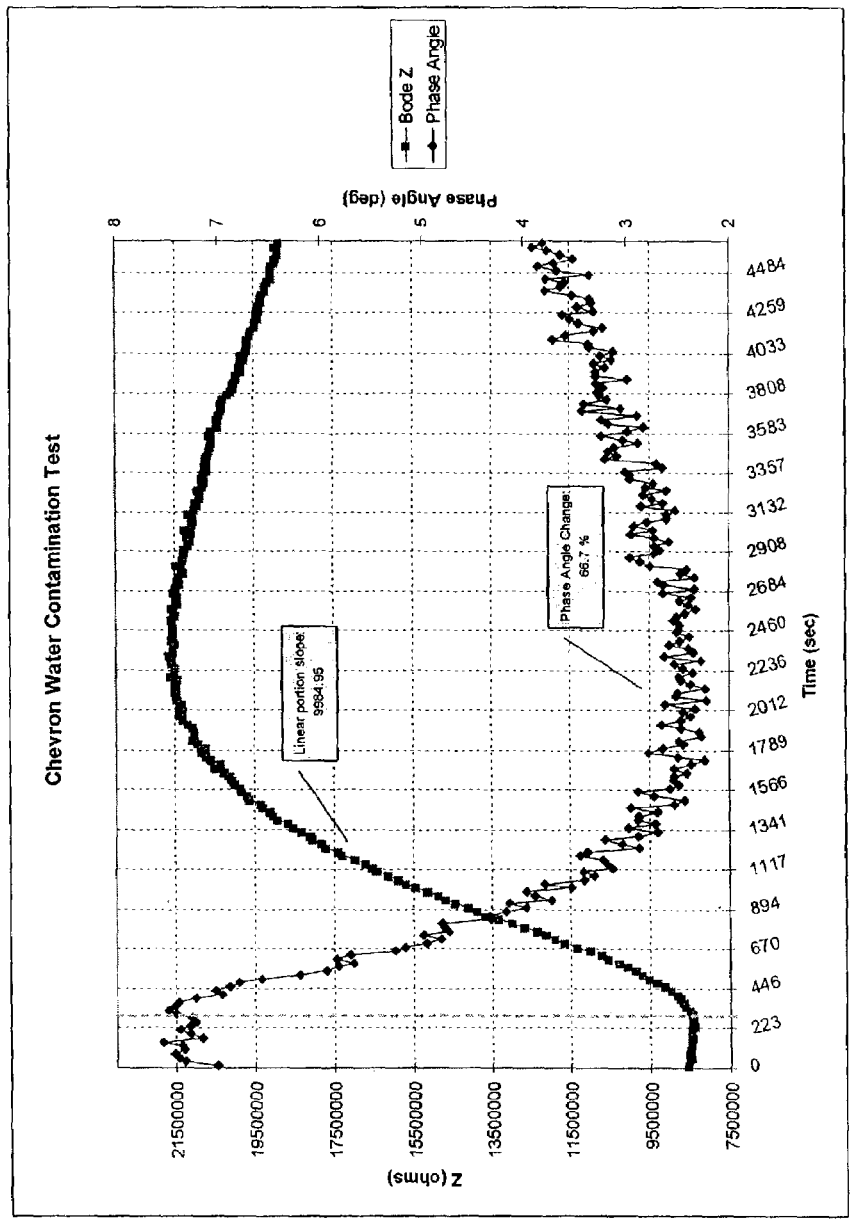
FIG. 12 – Plot of the Impedance Output Indication from Planar Sensor Structure for Water Contamination in Real-time

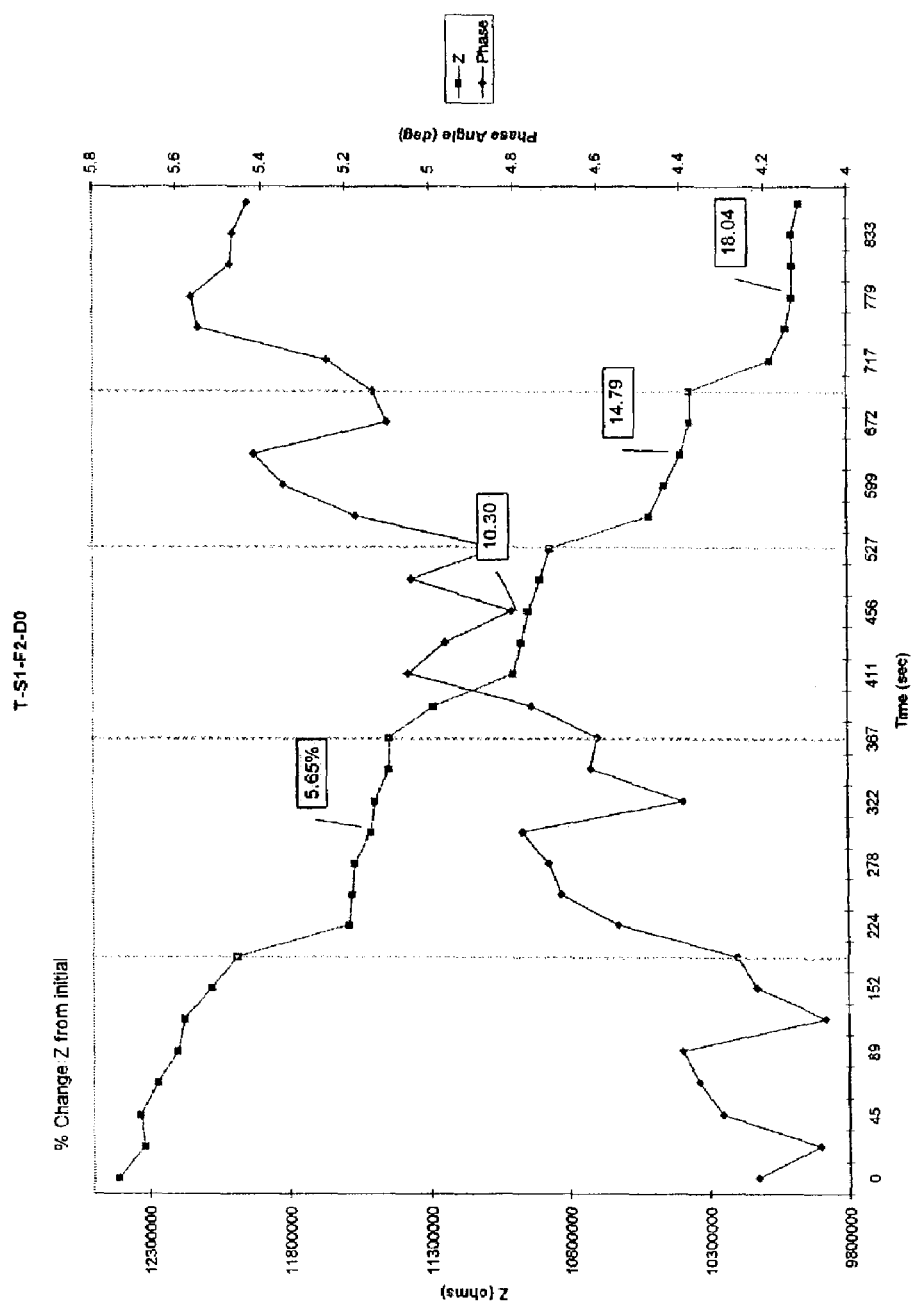
FIG. 13 – Magnitude Impedance „Z„ and Phase as a Function of Fuel Dilution Sensing in Real-time

|  | High Frequency Range | Middle Frequency Range | Low Frequency Range |
|---|---|---|---|
| Fresh Pennzoil | 648 | 38,832 | 251,350,858 |
| Used @ 3900 miles | 611 | 34,489 | 945,761,865 |
| % Change | 6% | 13% | 275% |

FIG. 14 – Magnitude Impedance „Z„ as a Function of Oscillation Frequency

| Pennzoil Sample | % Blend | Sensor Output |
|---|---|---|
| H3D0 | 0 | 250 |
| H3D2 | 10 | 323 |
| H3D5 | 25 | 591 |
| H3D7 | 35 | 949 |
| H3D10 | 50 | 1174 |
| H3D12 | 60 | 1226 |
| H3D15 | 75 | 1462 |
| H3D17 | 85 | 1570 |
| H3D20 | 100 | 1771 |

FIG. 15 – Magnitude Impedance "Z" as a Function of Oil Quality

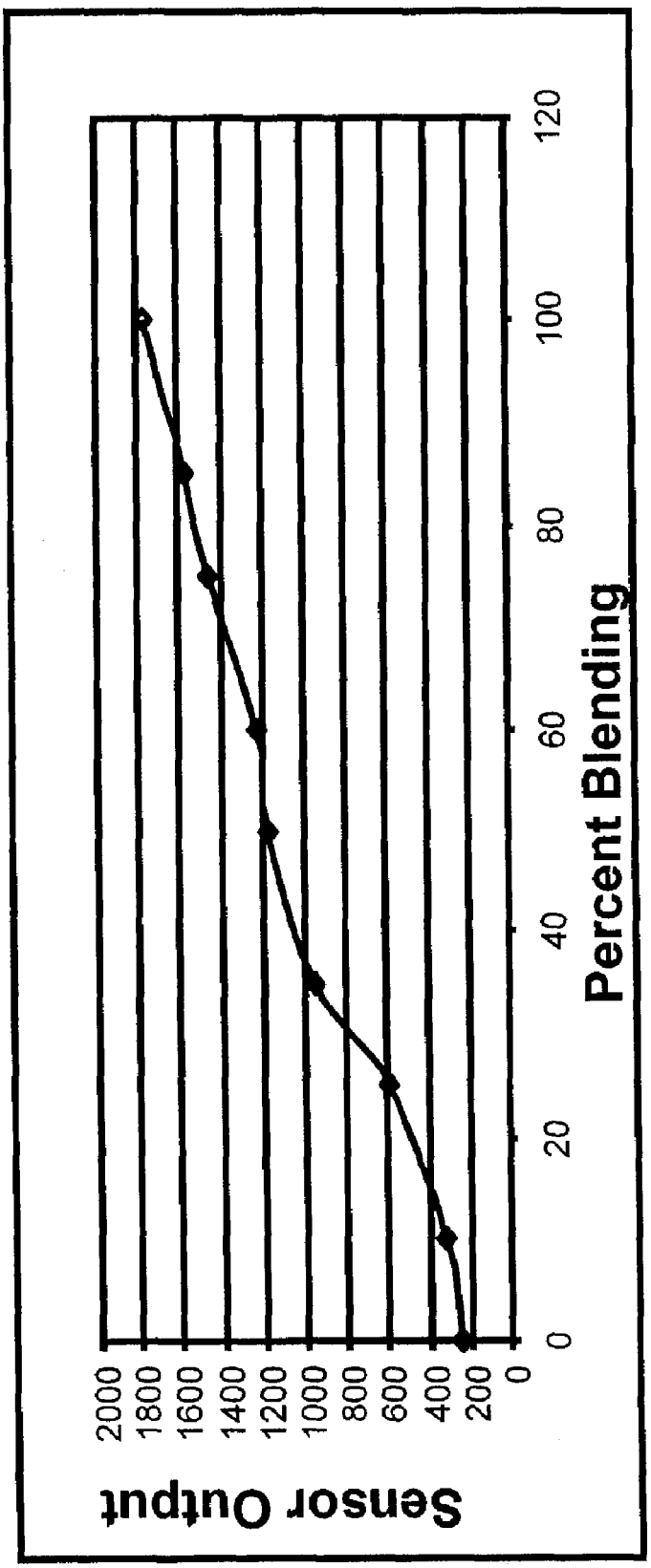
FIG. 16 – Plot of the Impedance Output Indication for Fresh, Blended, and Degraded Oil Samples

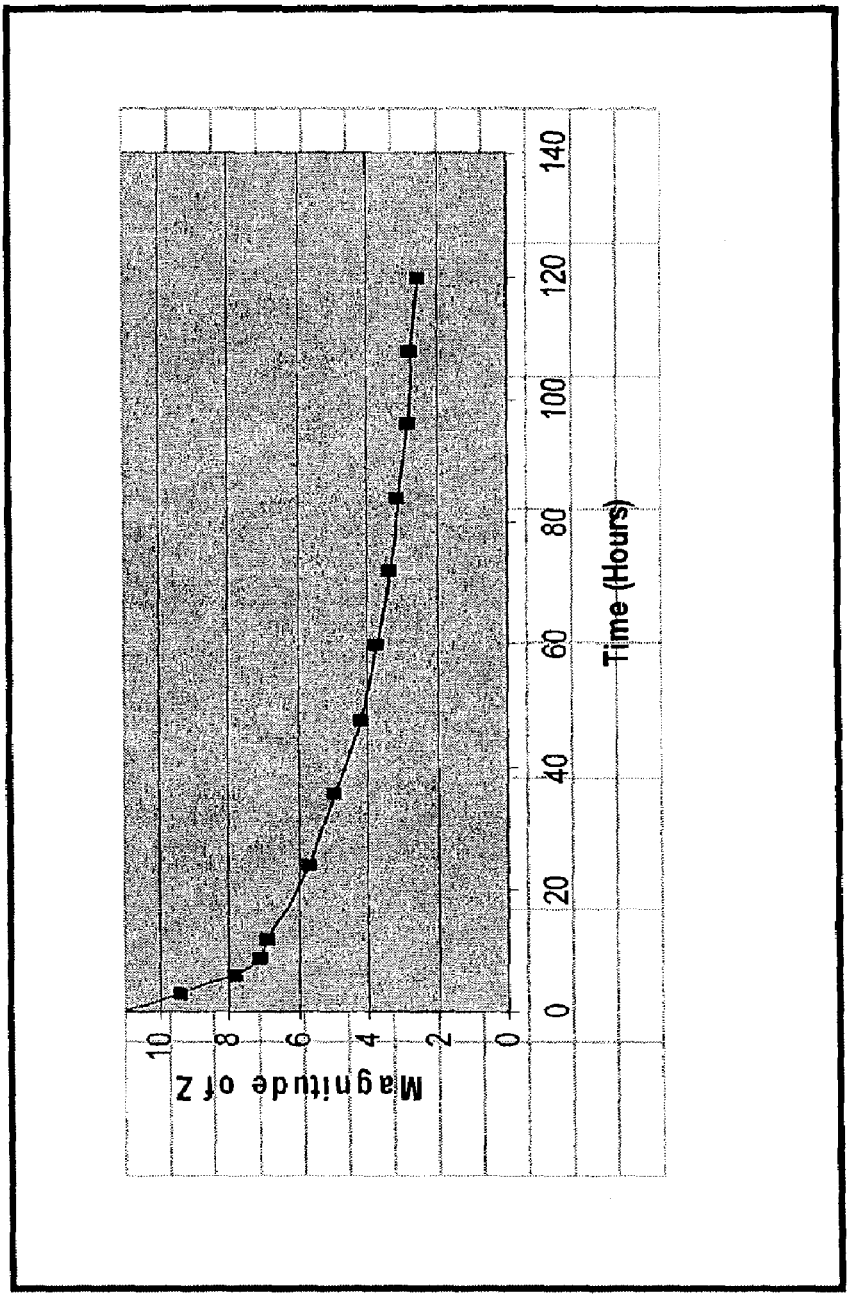
FIG. 17 – Plot of the Impedance Output Indication for a Laboratory-stressed Oil Sample at 320°F

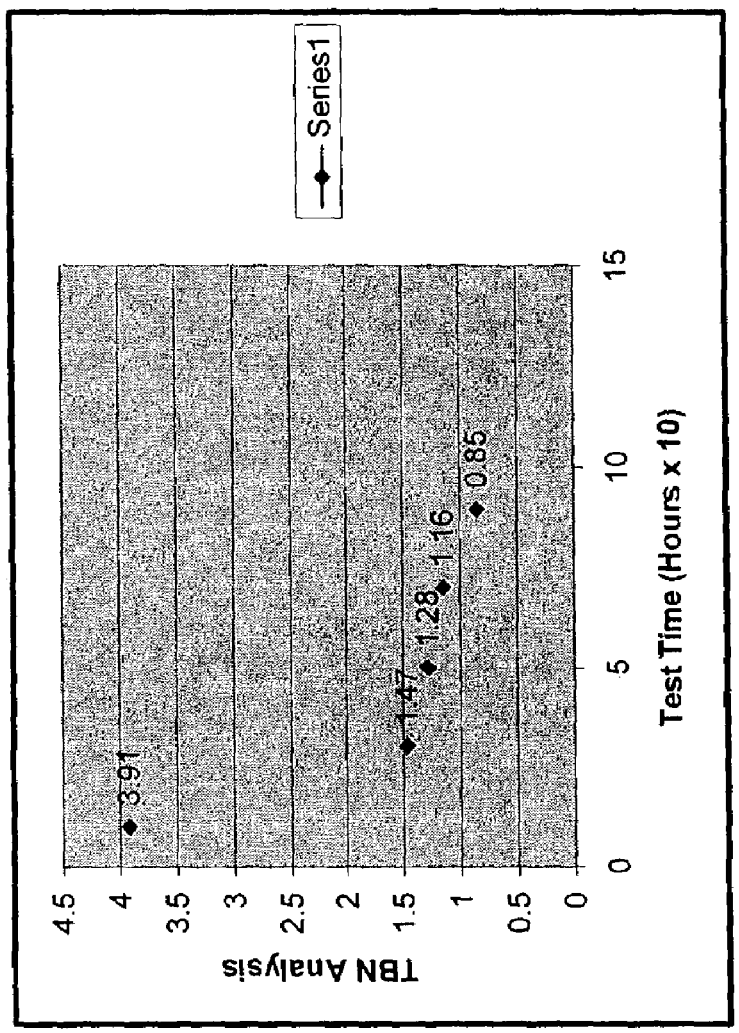
FIG. 18 – Total Base Number Plotted as a Function of Stress Time at 320°F

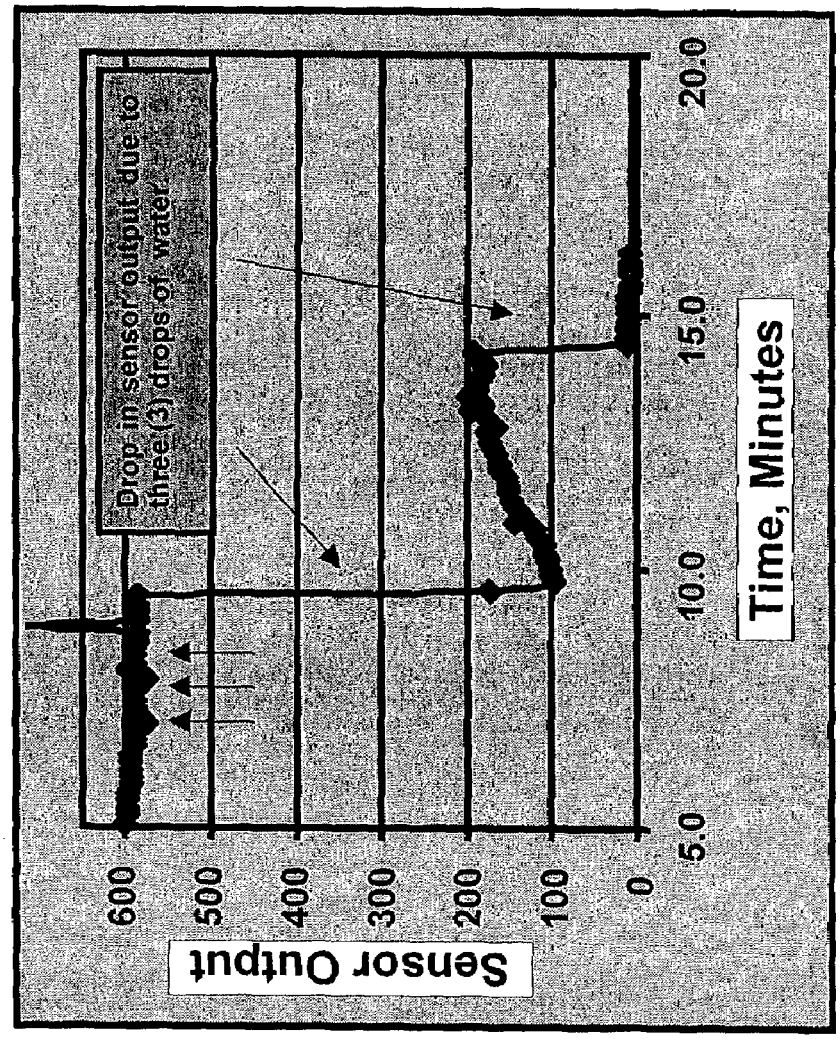
FIG. 19 – Plot of the Impedance Output Indication for Water Contamination in Real-time

ON-LINE OIL CONDITION SENSOR SYSTEM FOR ROTATING AND RECIPROCATING MACHINERY

CROSS REFERENCE TO RELATED APPLICATION

This application hereby incorporates by reference the contents of and claims priority to U.S. provisional application Ser. No. 60/342,686 filed Dec. 20, 2001.

FIELD OF THE INVENTION

The present invention relates generally to a method and an in-situ sensing system for detecting oil degradation, water contamination, and fuel dilution in operational engine oils, and, more particularly, to a method and on-line monitoring system for evaluating oil degradation, water contamination, and fuel dilution in real-time for internal combustion engine oils by an electrochemical impedance analysis technique.

BACKGROUND OF THE INVENTION

It is well known that engine oils become degraded with engine operation and time, eventually leading to increased heat, decreased performance, excessive wear, and possible component failure. Equally well understood is the fact that oil changes, as a preventive maintenance process, must be properly scheduled in order to prevent the undesirable consequences of using an oil beyond its effective useful life. Toward this end, conservatively scheduled oil change intervals are widely practiced so that lubricants with an expended useful life are not left in service to the point at which excessive wear is imminent. From a fundamental standpoint, however, oil changes based on a fixed number of engine hours or miles elapsed from a previous change rarely result in an optimal maintenance interval. While this situation to the private automobile operator is of little significance from either a financial or operational point of view, the same cannot be said for large commercial fleets or expensive machinery applications. In fact, the resultant effects of ill-timed oil changes can result in substantial, and sometimes major, unforeseen costs to nearly any organization that concerns itself with the commercial operation of various heavy equipment platforms. Frequent oil changes are indeed an excellent way to extend the life of an engine, but it's possible to change to often where the extra expense is there but the benefits to the engine are not. Aside from impacting the environment, such premature oil changes inevitably produce excessive and unnecessary costs for both labor and materials alike. They further result in decreased operational readiness and increased disposal costs as well. On the other hand, oil changes that are too late can result in even greater costs due to the need for increased engine maintenance caused by excessively degraded oils. Apart from length of service issues, unanticipated oil changes can also be required for problematic and certainly more serious circumstances that can prevail in operational engine oils.

It is in this context that one of the most critical maintenance tasks facing heavy equipment operators is determining exactly when to change lubricants. As such, oil analysis has been applied for many decades as a powerful management tool for optimizing fluid change intervals and predicting impending mechanical failure through the examination of used oil samples. In most machinery, the beginnings of a breakdown occur thousands of miles or hundreds of hours before the breakdown itself. Signs of potential trouble usually appear first in the oil, the equipment's lifeblood. Just as a human blood sample can reveal much about an individual's health, oil analysis can afford critical insight not only on the optimum point at which oils should be changed, but when mechanical repairs might be necessary as well.

Rotating and reciprocating engine systems require a wide variety of organic and synthetic lubricating fluids to operate effectively. Lubricants are used in operating equipment to reduce friction between moving components and to transfer heat and debris from the wetted surfaces of the lubricated components. Lubricating oils for reciprocating internal combustion engines are referred to as motor or crankcase oils. The vast majority of these oils are made from a mineral oil base refined from naturally-occurring crude petroleum. Motor oils based on synthetic stocks are also available but are less commonly used due to their high price. Crankcase oils differ from other lubricating oils in that they necessarily contain extensive additive packages. During use, crankcase oils experience thermal, oxidative, and other environmental stresses that accelerate their degradation. To slow the rate of this degradation, different types of oil-soluble chemicals (e.g.—detergents, dispersants, antioxidant/antiwear agents, etc.) are blended with the base stock of an oil to enhance and sustain its desirable qualities. Such chemicals, respectively, can serve to not only prevent the corrosion of metal surfaces and the formation/deposition of insoluble materials, but they can also inhibit oxidation of the oil base stock and reduce mechanical wear as well. Nevertheless, these additive species are gradually depleted with engine operating time, and they eventually become ineffective at neutralizing acids and controlling oxidation.

This is particularly important with respect to the antioxidant compounds that are formulated in crankcase oils (e.g.—zinc dialkyldithiophosphate, ZDTP, etc.). In fact, as engine oil oxidation is the most common means of lubricant degradation, the rate at which these antioxidants are spent largely determines the remaining useful life of a lubricant in service. Once one or more of these multifunctional additives and their decomposition products are depleted to roughly 10–20% of their original concentration, the desired oil qualities associated with these chemical additives can begin a sudden and dramatic decline. With the depletion of the oil's antioxidant package, the viscosity, total acid number (TAN), and metallic wear levels normally increase, sometimes rapidly. Eventually, this allows large changes to occur in the physical properties of the lubricant's base stock wherein the lubricant is no longer capable of protecting the engine and its useful life ends. Thus, if the respective fluid is left in service and this oil degradation mechanism progresses, continued equipment operation will inevitably lead to severe engine component damage, and possibly failure.

In addition, there are other operating characteristics associated with certain engine platforms where the continuous assessment of oxidation levels can afford real opportunities for substantial improvements in key asset utilization. In the case of diesel locomotive engines, for instance, engine sumps are topped off frequently to replace oil lost through consumption. These oil replenishments between drains strengthen additive packages and thus slow the rate of thermal-oxidative breakdown during subsequent engine operation. Therefore, it has been recognized that "trend-line" information on an oil's progressive deterioration and revitalization (a subsequent improvement in the data collected) can provide key insight on the rate at which fresh oil is added to the respective engine system. Accordingly, this can help a variety of equipment operators to maximize the efficiency of their preventive maintenance activities not only in terms of potentially extending fluid change intervals, but particularly from the standpoint of identifying problematic engines within an overall fleet that require excessive additions of oil (due to consumption or "burn-off" as a result of bad or failing piston rings).

Whether due to either natural or problematic phenomena, lubricating fluids can also be exposed to various occurrences of water contamination while in service. Natural occurrences of water contamination in lubricating oils are primarily a function of three related processes. They include: (1) a diffusion of vapor water from the atmosphere (which is proportional to relative humidity, temperature, and polar compounds concentration, (2) water condensation promoted by cyclic variations of temperature, and (3) aging of the oil—that is, oxidation. Under such engine operating conditions involving cyclic variations of temperature, water vapor from the atmosphere is carried with the combustion products into the crankcase and thus can condense there. This diffusion and condensation process can further be enhanced due to poor crankcase ventilation and excessively worn piston rings which results in added blow-by contamination from vapor water. Moreover, empirical evidence indicates a preponderance of water-related problems associated with equipment operating conditions that include (1) primarily short-trip driving and (2) low-temperature operations such as extensive soaking & idling modes, as is often the case with diesel locomotive applications. There is also evidence, nevertheless, that problems associated with water contamination processes of this nature can fortunately be mitigated with the various detergent and dispersant additives that are formulated in today's engine oils.

There are potentially serious operational conditions, however, that, if allowed to persist, can result in catastrophic engine failure due to problematic occurrences of water contamination. Again in the case of internal combustion engines, for instance, blown engine head gaskets, other seal failures, or cracked water jackets can result in either intermittent coolant leakage or even a continuous ingress of water into the oil. The presence of water in engine oils, whether in the dissolved or free water form (i.e.—the actual molecules themselves are present), can cause a significant reduction in the operating life of a fluid. Water is detrimental to lubrication both physically and chemically. It not only catalyzes oil oxidation and promotes the formation of dangerous metal corroding acids, but it reacts with, or precipitates, the chemical additives in oils as well. The emulsion that results from the respective hydrolysis process can also cause oil filters to plug, thus potentially causing bearing seizure on crankshafts. Water further corrodes many common tribological metals at the same time. For example, water can react with ferrous alloys to form rust which creates solid debris in the oil and pits the metal surfaces of the engine, potentially initiating contact fatigue in engine bearings.

While such an anomaly presents a certain, universal problem for all reciprocating gasoline or diesel internal combustion engines, water contamination of crankcase oils in diesel locomotive engines is a particularly serious problem. The primary elements that support this condition are twofold. First, there are the physical elements that prevail with diesel locomotive engine operation. This applies to not only the actual (i.e.—large) quantities of water used as a coolant in engines of such enormous displacement, but the magnitude to which the production of 4,000 horsepower (which is common in engines of this type) creates intense, earth-shaking vibration. Secondly, the attendant mechanical elements associated with locomotive engine and cooling system designs must be considered as well. The respective internal engine component tolerances are not only in essence "loose", but large and extensive lengths of piping, or conduit, surround the engine for the delivery of water to key portions of the engine. Thus, when each of the aforementioned elements are working in concert with one another (albeit to the potential detriment of the system), the problems associated with frequent & excessive water contamination processes are imminent, if not dangerous altogether.

In the absence of a spark ignition process for diesel fuel combustion, large quantities of water that may enter one or more of the engine's combustion chambers cannot be compressed. As such, an uplifting piston—on the compression stroke of the diesel engine—could potentially be forcefully expelled through its respective cylinder wall and out of the engine block.

Lubricating oils are also susceptible to contamination from fuel. This is particularly relevant in the case of diesel internal combustion engines that, unlike spark-ignition gasoline engines, operate via a compression-ignition process that requires the inclusion of excess amounts of fuel in the combustion chamber for detonation. The oil, as part of its intended role, must provide a barrier against surface contact, provide sealing from combustion by-products at the ring layer, and transfer heat from the engine for cooling. Thus, if a degrading engine oil becomes excessively diluted due to a problematic occurrence of fuel contamination, its ability to perform these functions can be reduced significantly. As fuel thins the engine oil, the fluid's viscosity decreases and this typically leads to increased engine wear. This process, at a bare minimum, will further result in overheating and, in some cases, even engine failure. Several potential causes of fuel dilution include: (1) leaking/defective injectors, (2) excessive idling, (3) incomplete combustion, (4) worn liners/rings, and (5) poor fuel quality. Specific tests for liquid fuel contamination should, without question, be an essential part of any used oil analysis program. This is especially true with today's engines that are being operated with light, energy-saving multigrade oils, as these oils allow operation very close to the critical minimum oil film thickness. In this case, relatively little fuel dilution can result in catastrophic damage.

With today's industrial sector organizations, used oil analysis programs play a major role in the majority of the preventive maintenance programs that are tied to the commercial operation of various engine and machinery platforms. The overriding problem, however, is that the major portion of today's technology for performing oil analysis resides in the professional fluids analysis laboratory. Granted, commercial laboratories can provide a battery of tests which, taken together, provide a truly comprehensive picture of oil and engine condition. Inherently, the essential problem With oil condition monitoring via off-site, laboratory testing is that the monitoring is neither continuous nor immediate. Equipment operators are confronted with the inconvenience and untimeliness associated with collecting oil samples for lab analysis. Expensive and complicated procedures often result in condition reports being delivered too late to rectify a problem. More than once, a machine has failed catastrophically before the cautionary notice from the lab reached the operator.

It can therefore be seen that the capability to continuously monitor crankcase oils for thermal-oxidative breakdown, water contamination, and fuel dilution could enable fluid changes to be based upon the actual condition of the lubricant and not on the basis of a fixed schedule. Such capacities for oil analysis at the in-situ level could not only eliminate the need for oil sampling, but they could further enable equipment operators to extend fluid change intervals, thereby affording a savings in material and labor costs as well.

Moreover, the detection of abnormal levels of water, fuel, or thermal-oxidative breakdown in engine oils can also be a signal of future equipment failure. This in turn can allow mechanical repairs and fluid changes to be made before critical, and sometimes catastrophic, levels of deterioration are reached. By establishing exact, engine-specific oil change intervals for any given duty cycle, heavy equipment and machinery operators could maximize equipment protection and cost efficiency at the same time.

There are known electrical-type sensor devices that, with varying forms of associated apparatus, have been developed for on-line monitoring of lubricating oils in operational engine systems. To date, however, these systems tend to exhibit distinct drawbacks with respect to either overall sensitivity, ambiguous responses over time or with changing operating conditions, or just poorly-conceived device designs that result in similar inadequacies.

For example, U.S. Pat. Nos. 4,733,556 and 5,540,086 of Meitzler and Kyong et al., respectively, disclose oil deterioration detection methods, or devices, that employ electrical capacitance-type transducers with an alternating current (AC) carrier voltage source for excitation to monitor changes in the dielectric constant of operational engine oils. Both patents indicate that, based upon experiments performed, there is a strong correlation between the time variation with usage of oil dielectric constant and oil viscosity. These patents provide a method and apparatus for comparing the dielectric constant of a given engine oil with that of a like unused oil in the same temperature environment in order to determine when the lubricating oil has deteriorated by acquiring a viscosity value predetermined as being too high. In operation, however, these capacitance-based methods employ relatively high oscillation frequencies that, over the range of 50–100 KHz, produce a total approximate change in oil dielectric constant of only 10% over the useful life of a candidate engine oil.

In addition, other systems have also been developed and found operationally acceptable as devices for indicating the overall condition of lubricating oils. For instance, U.S. Pat. No. 5,274,335 of Wang et al. discloses an oil deterioration and water contamination sensor system wherein measurements of the electrical admittance (the reciprocal of electrical impedance) in oils are used to provide an indication of overall oil quality. In operation, however, the respective sensing device employed in this resistance-based method is supplied with an AC triangular waveform potential that, at ±5 V and 400 V/sec results in an oil-condition-dependent current that is inconsistent, or ambiguous, with concern to tracking oil condition with continued engine operating time. In fact, it is noted in the U.S. Pat. No. 5,200,027 of Lee et al. that both parallel-plate and interdigitated-type (two-electrode) sensors have associated problems in differentiating between new and used oil, because both oils have large concentrations of chemically reactive species that produce conflicting results. Therefore, to overcome this undesirable performance (deemed a "selectivity problem"), Lee et al. discloses in the latter patent that special sensor treatments (the sole privilege claimed) are required to overcome the ambiguous "V" shaped sensor output that was realized from the system employed earlier in said U.S. Pat. No. 5,274,335. The processes required to produce the respective sensor structures, however, are relatively complex and require special materials and significant work to obtain the desired result.

Additional attempts have also been made by others to employ electrical sensor principles for characterizing the condition of engine oils in motor vehicle applications. Work published by Kaden, et al., (On-Line System for Lubrication Diagnostics, MTZ Worldwide, March 2000, pg. 8–11) for instance, discloses several different measurement techniques (although with several different sensing devices) that are applied to the in-situ measurement of water and/or fuel contamination, the alkalinity of oils, as well as wear metal particles. In operation, however, several inconsistencies were noted with each of the employed methods and/or devices for either detecting, or properly characterizing, the particular device's intended analytical parameter. It was recorded, for instance, that an impedance-based method for detecting water and fuel in fresh oils exhibited several inconsistencies as a function of the test vehicle speed. In particular, it was noted that the respective impedance response decreased with increasing engine speed, a result that was suggested to be attributable to a "systematic deviation of the oil temperature in the oil sump from that in the measuring cell." The influences of blow-by gases were also studied to establish what effects this might have on the respective impedance-based measurement strategy. While higher impedance values were expected wit the increased proportion of combustion gases in the oil medium, the produced impedance values did not confirm this hypothesis. Moreover, additional tests were carried out to investigate whether potentiometric-based measurements (pH) could be made successfully in operational motor oils—particularly in the context of the desirability to show how such a measurement (and its associated sensor) might correlate with laboratory values for Total Base Number (TBN). What was learned from these tests, however, was that the candidate potentiometric sensor devices displayed irreversible instabilities as the oil temperature increased for the fresh and used oils tested. It is with findings such as these in mind that the aforementioned drawbacks are worth noting. Whether due to the notion of ill-conceived product designs or inconsistent sensor responses, there is certainly room for improvement in the overall strategy for providing a reliable, real-time indication of operational engine oil quality.

Furthermore, the small majority of competing systems patented to date are not only in absence of dedicated signal analyzing devices, but they are further without a user-friendly interface (not to mention graphical) for timely display of critical information. The intrinsic value, even fundamentally speaking, of the analytical information provided to equipment operators is insufficient as well, if not grossly underrepresented altogether. Competing product strategies employed to date have yet to produce a complete instrument package, or "system", that can afford real analytical value on an operational basis.

There has yet to be realized a commercially acceptable on-line apparatus, or system, that—by monitoring the aforementioned root problem oil parameters—can enable equipment operators to readily establish optimal oil condition maintenance practices or detect potentially serious mechanical engine problems. Therefore, there remains a need for a method and apparatus, or complete system, that can simultaneously detect thermal-oxidative oil degradation, water contamination, and fuel dilution in hydrocarbon and synthetic lubricating oils, particularly from a single, relatively simple sensing device for internal combustion engines.

SUMMARY OF THE INVENTION

The invention disclosed herein solves this need by providing comprehensive electrochemical measurement and data analysis techniques that, with an associated sensing device, provide a complete, quantitative assessment of oil degradation, water contamination, and fuel dilution levels in a wide variety of internal combustion engine oils.

As already highlighted, operational engine lubricants experience thermal, oxidative, and other environmental stresses that cause them to break down. It is for this reason that the different types of detergents, antioxidants, and anti-wear/corrosion agents are added to base oils to sustain their performance. The thermal and oxidative breakdown of engine oils, in the presence of these additives, thus leads to the formation of various ionic species in the oil medium. The oil degradation process further leads to the formation of acidic compounds such as nitric and sulfuric acids in the oil basestock, due primarily to combustion blow-by gases. In this case, with these ionic species and acidic compounds affecting the electrical properties of oils, there is a favorable availability of reactants in the oil that can be measured electrochemically. In addition, in the event of a coolant leak, highly polar liquids that come into contact with the oil medium will, in essence, reduce the ohmic resistance of the oil (particularly at the interfacial area of said electrodes and the oil medium).

As a general rule, electrochemical measurement techniques are experimental methods developed to study the physical and chemical phenomena associated with electron transfer at the interface of an electrode and solution. The objective is to obtain either analytical or fundamental information regarding the constituent electroactive species in solution, which in the case at hand are the various oil additives and oxidation species that prevail in either new and/or used oils. Investigations involving fundamental electrode designs are an additionally significant part of electrochemical measurement strategies. The physical and chemical phenomena important in electrode-based processes generally occur very close to the electrode surface (usually within a few microns). Therefore, the charge transfer of the chemical additives and degradation species involved in an electrochemically-induced process (i.e.—to and from the bulk oil) can be a key aspect of analysis. It has been determined in accordance with the current invention that—through fundamental investigation of particular electrode characteristics—distinct sensor configurations can be coupled with complimentary electrochemical impedance spectroscopy (EIS) techniques to obtain important information on the condition of a wide variety of conductivity-resistant engine oils.

In accordance with a specific illustrative embodiment of the current invention, a two-electrode sensor configuration can be immersed in the oil medium to produce an oil-condition-dependent response from the applied electrochemical impedance analysis technique. Constructed such that it can be directly mounted within the oil reservoir of an internal combustion engine, for instance, the respective sensing device (planar-type) includes a suitable mechanical housing sub-assembly and a closely spaced electrode pair disposed within the housing and extending outwardly therefrom. The dual-trace-type sensor configuration with the dielectric lubricant contained between the identical electrode pair thereby defines the electrochemical sensor output-impedance-circuit used to provide an indication of the operational oil's quality or deterioration.

In a further aspect of the present invention for monitoring operational engine oils, a sinusoidal voltage waveform (at a specific amplitude) is applied across the respective two-electrode sensor configuration to produce a frequency dependent current through the oil-electrode system. With electronic instrument means for producing the respective AC waveform connected to the two-electrode sensor, a distinct low frequency excitation signal is employed whereby information on the resistance and capacitance of the degraded fluid can be utilized to ultimately afford key information on the specific condition of the oil under test.

In accordance with another aspect of the invention, precisely-defined methods of electrochemical data analysis can further be employed to accurately & thoroughly characterize the electrochemical impedance properties (complex impedance) of the two-electrode system. More specifically, key data plot representations of the collected voltage and current responses can be engaged as a principal platform of analysis to precisely determine a specific oscillation frequency at which the overall sensitivity of said impedance measurement can be optimized. Ultimately, what can be produced from the respective impedance analysis platform are key data points on the magnitude impedance |Z| of said oil lubricant.

Thus, it is with the respective distinct method of electrochemical data analysis that the produced information (at each distinct frequency) can, in its entirety, afford quantitative, analytical-quality data for not only determining an oil's operational acceptance, but even predicting its eventual condemnation. As the resultant data points are appropriately processed and subsequently stored in computer memory, the calculated magnitude impedance |Z| of the oil medium (along with other derivatives of said complex impedance calculation) can serve as a specific indication of the attendant degradation, water contamination, and fuel dilution levels in operational engine oils.

In a further aspect of the present invention, the respective sensing device can include two closely parallel electrodes with a gap between them of just less than or equal to about 150 microns, or 0.15 mm. Each electrode can be fabricated to have a thickness of between 0.006 and 0.012 inches, or 6 and 12 mils, respectively. With standard photolithography and etching, for instance, specific sensing devices in accordance with this invention can further be produced whereby various dual-trace-type electrode geometries afford sensor areas on the order of one to three square centimeters. Additional sensor fabrication steps in accordance with the invention herein include the appropriate application of various metallization layers to the closely parallel electrodes to enable a longer service life and ensure overall stability at high engine oil temperatures.

In still another aspect of the present invention, the resultant oil degradation, water contamination, and fuel dilution sensor system will include appropriately stored algorithms in software that can accurately adjust the respective electrochemical impedance measurements to compensate for the effects of engine oil temperature changes.

It has further been found that electrochemical impedance measurement and data analysis techniques in accordance with the present invention can enable sensor-driven diagnostics & prognostics capabilities for oil degradation, water contamination, and fuel dilution levels in operational engine oils. The invention is based in part on the discovery that, as electrochemical data for such root problem oil parameters is appropriately correlated with physical and chemical data provided by several laboratory tests, diagnostics & prognostics capabilities in accordance with the present invention can, in essence, establish a "fingerprint" or "signature" for the attendant degradation and contamination phenomena in various engine oils.

Some of the advantages associated with the sensor system and method of the present invention include the following:

First, the application of low-frequency measurement techniques results in a sensor system that, from a scientific or fundamental perspective, is considerably more robust than the prior art systems referenced above. The primary advantage associated with the respective electrochemical impedance analysis platform is that a wealth of analytical data can be gained from a single sensor device in real-time.

It is with such low-frequency measurement techniques that particularly sensitive measurements, and highly predictable as well, can be made simultaneously across most of the vital, determinant parameters for oil analysis. Other distinct advantages associated with said impedance measurement platform include desirable performance characteristics such as expanded dynamic range and enhanced resolution.

The respective low frequency impedance analysis platform further results in quantitative electronic output that readily correlates in a direct and straightforward manner to well-established laboratory analyses such as TAN/TBN, Viscosity, Infrared Spectroscopy, and Differential Scanning Calorimetry. In addition, again unlike the prior art discussed above, such low frequency measurements can accurately identify (and perhaps quantify) specific water-in-oil disparities not only for excessive contamination levels, but even for insidious amounts less than 0.1%.

There are additional advantages to the present invention that are directly linked to the capability of the respective low frequency impedance measurements to produce sensor responses that are sensitive to the actual reactivity of the aforementioned chemical additives employed in oils. As outlined above, these are the additives that, by their very design, are precisely formulated to either rapidly combat acids accumulation, or rather methodically stave off excessive oxidation. When multifunctional calcium-based additives are the predominate compounds at work, there can be seen two distinct reactions: first, a rapid decrease; and second, a slow, yet continuing reaction. For zinc-based additive packages, on the other hand, the respective first order depletion reaction is a gradual one; while the second order reaction is deliberate and, "at days end," disappears altogether. This is substantially the same behavior that is exhibited with said low frequency impedance measurements described above. Thus, it is from these distinctive and highly discriminative reactionary pathways that it is proposed the aforementioned incomparable sensor responses are derived. Quite unlike the aforementioned prior art electrical property sensor devices (where only minimal and often ambiguous changes of 10% are realized), the novel impedance analysis technique disclosed herein is sensitive not to the specific dielectric constant of the oil, but to the actual "remaining presence" or "attendant depletion" of the employed additive compounds themselves (e.g.—continuously-solubilizing detergents and/or decomposing zinc antioxidants, respectively).

By employing high-input-impedance circuitry directly on said sensor substrate (or in its housing), electronic signal conditioning (or buffering) can be achieved for superior performance in challenging environments of EMI/RFI, temperature variation, humidity, vibration, etc. Through a specific illustrative embodiment of the respective buffer circuits, it is anticipated that, with such buffer circuits "built-in," real advantages can be attained in terms of desirable performance characteristics such as: (1) stability and/or linearity, and (2) overall repeatability.

In accordance with another embodiment of the present invention, the aforementioned principal impedance analysis platform inherently affords analytically superior measurement techniques enabling self-diagnostics capabilities for identifying non-oil-related anomalies such as a shorted sensor, failed connection, broken wire, etc.

The present invention includes other advantages related to the employment of state-of-the art digital electronics on-board. With an electronic instrument package and ample memory installed, invaluable self-calibration capabilities can be realized for error-free application across different brands and types of engine oils (hydrocarbon, semi-synthetic, or full-synthetic). The respective microprocessor-based instrument package also allows for automatic temperature compensation over varying operational conditions. And, again unlike the prior art systems referenced above, the respective instrument system, along with its "intelligent" algorithms embedded in software, can inherently afford a rapid response for the particular oil condition being sensed—whether normal or problematic. Built-in microprocessors can further be used for advanced system control where, with multi-tasking capabilities, one analysis can be run while data acquisition for another is ongoing. As such, vital information can be obtained instantly on any excessive thermal-oxidative conditions or contamination problems that might prevail.

Other advantages are associated with the present invention in that, by employing analog & digital electronic circuit designs both "in-sensor" and "on-board," real advantages can be attained in terms of highly robust data analysis routines that afford distinct, quantitative precision in the overall measurement performed. The employment of digital electronics on-board can also provide "intelligent" display capabilities for user specified, value-added options as well. Moreover, digital circuit designs dedicated to the respective impedance measurements can further enable direct compatibility (i.e.—matching source and object code) for an industry-standard SAE J1708/1587 serial data link built-in. Inherently, the resultant advantages of such digital circuit designs are immediate "plug-and-play"-type capabilities for a bidirectional, serial communications link between existing truck components. This allows direct transmission of electronic signals—that is, LED activation and/or diagnostic flash codes—to existing in-cab display devices.

Additional advantages are a direct result of the aforementioned low frequency measurement techniques and high input impedance circuit designs. From a manufacturability standpoint, highly robust sensor devices can be produced from practical, straightforward production methods (i.e.—batch fabrication) that afford a more desirable per-unit cost. Sensing devices in accordance with the present invention are also relatively small in size, readily facilitate on-line monitoring, have a short response time, and remain mechanically sound under harsh, in-service conditions. Finally, it has further been found that sensing devices in accordance with the invention herein are not only easy to install, but can be readily and inexpensively replaced—whether for retrofit or OEM-level applications.

BRIEF DESCRIPTION OF THE DRAWINGS

The invention will now be described in connection with the accompanying illustrative drawings, schematics, diagrams, data plots, tables, and/or graphs.

FIG. 1 is a schematic view of a parallel planar-type oil sensing device in accordance with the present invention;

FIG. 2 is a schematic view of an interdigitated planar-type oil sensing device in accordance with the present invention;

FIG. 3 is a schematic view of a concentric planar-type oil sensing device in accordance with the present invention;

FIG. 4 is a schematic view of a planar-type, three-electrode-configured oil sensing device in accordance with the present invention;

FIG. 5 is a diagrammatic rendering of an equivalent circuit model for a planar-type oil sensing device in accordance with the present invention;

FIG. 6 is a plot illustrating the logarithm of the magnitude of the impedance |Z| versus the logarithm of frequency (f) for a tested lubricant as a function of voltage and time in practicing the method for characterizing new or used oils in accordance with the present invention;

FIG. 7 is a plot illustrating the phase angle (θ) between the AC potential and current versus the logarithm of frequency (f) for a tested lubricant as a function of voltage and time in practicing the method for characterizing new or used oils in accordance with the present invention;

FIG. 8 is a plot illustrating the imaginary impedance component versus the real impedance component at a given frequency for a tested lubricant as a function of voltage and time in practicing the method for characterizing new or used oils in accordance with the present invention;

FIG. 9 is a plot illustrating the imaginary impedance component versus the real impedance component at a given frequency for several tested lubricants as a function of voltage and time in practicing the method for characterizing new or used oils in accordance with the present invention;

FIG. 10 is a plot illustrating the logarithm of the magnitude of the impedance |Z| versus the logarithm of frequency (f) for a tested lubricant as a function of voltage and time in practicing the method for characterizing water contamination in new or used oils in accordance with the present invention;

FIG. 11 is a plot illustrating a two-wire sensor's output indication impedance |Z| and phase angle in practicing the method for water contamination at room temperature over time in degraded oil;

FIG. 12 is a plot illustrating the planar sensor's output indication impedance |Z| in practicing the method for water contamination at 140° F. over time in oil;

FIG. 13 is a plot illustrating the planar sensor's output indication impedance in practicing the method for fuel dilution in real-time at 140° F. in oil.

FIG. 14 is a table illustrating three comparison magnitude impedance |Z| output indications over a wide range of oscillation frequencies for a new and a used oil sample of common formulation at room temperature;

FIG. 15 is a table illustrating the sensor's output indication impedance (dual-wire-type) in practicing the method for detecting oil degradation at room temperature for a fresh sample, a degraded sample, and a series of blended samples;

FIG. 16 is a plot illustrating the sensor's output indication impedance in practicing the method for monitoring fresh, blended, and degraded oil samples at room temperature which is based on the data set forth in FIG. 19;

FIG. 17 is a plot illustrating the sensor's output indication impedance in practicing the method for monitoring oil degradation in real-time at 320° F. for a laboratory-stressed oil sample;

FIG. 18 is a graphical representation of the Total Base Number plotted as a function of stress time at 320° F. for a laboratory-stressed oil sample;

FIG. 19 is a plot illustrating the two-wire sensor's output indication impedance in practicing the method for water contamination in real-time at room temperature in degraded oil;

DESCRIPTION OF EMBODIMENTS OF THE INVENTION

Figure 20:
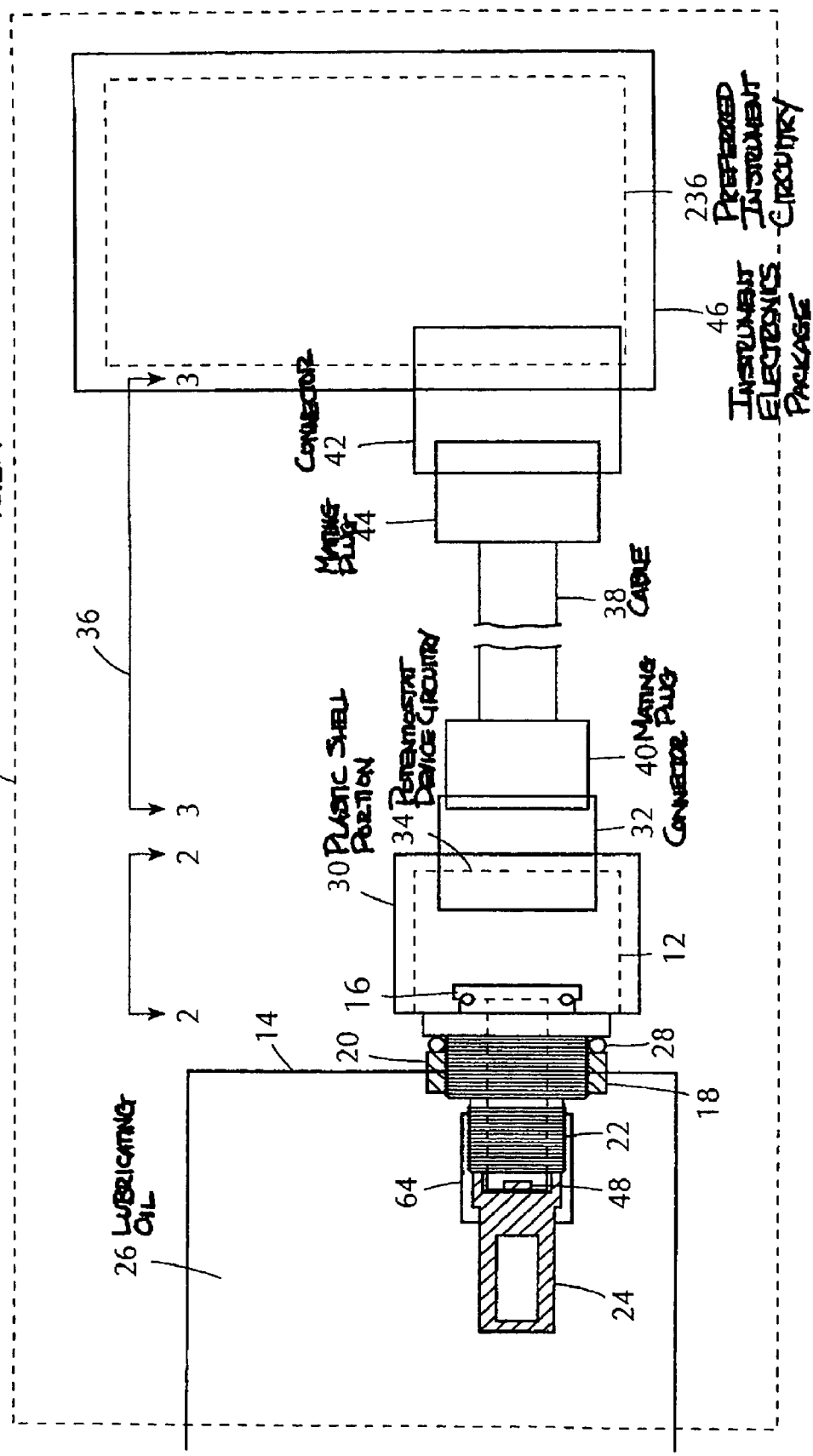
FIG. 20 illustrates in schematic form an in-situ, on-line oil condition monitoring system of the present invention.

FIGS. 1, 2, and 3 are schematic renderings of candidate planar-type, two-electrode sensor designs that, when packaged as complete devices, can be easily fitted within a wall of an internal combustion engine oil reservoir, such as the crankcase of a diesel locomotive engine. As shown in FIG. 4, a planar-type, three-electrode sensing devices can also be employed in practicing the invention for successfully characterizing the attendant degradation, water contamination, and fuel dilution levels in operational engine oils.

The sensing device can include two (or three) closely parallel electrodes with a gap between them of just less than or equal to about 150 microns, or 0.15 mm. Each electrode can be fabricated to have a thickness of between 0.006 and 0.012 inches, or 6 and 12 mils, respectively. With standard photolithography and etching, for instance, specific sensing devices in accordance with current invention can further be produced whereby various dual-trace-type electrode geometries afford sensor areas on the order of one to three square centimeters. Additional sensor fabrication steps include the appropriate application of various metallization layers to the closely parallel electrodes to enable a longer service life and ensure overall stability at high engine oil temperatures. For example, FIG. 1 illustrates a planar-type sensor device with two (2) electrodes in a straight, closely-parallel configuration. The respective line widths are between 0.004 and 0.012 inches, or 4 and 12 mils, and the line spaces range from 4 mils to 10 mils. FIG. 2 shows an interdigitated (IDT) configuration (such as electrode configuration 58 in FIG. 21) in which the respective two closely parallel electrodes have a gap between them of just less than or equal to about 150 microns, or 0.15 mm (also 6 mils). It is also preferred that the counter and working electrodes 72 and 74, respectively, are fabricated to have a thickness of between 0.006 and 0.012 inches, or 6 and 12 mils.

FIG. 3 illustrates a planar-type sensor device with two electrodes in a closely-parallel, concentric orientation. The two (2) closely parallel electrodes in this particular design also have a gap between them of just less than or equal to about 150 microns, or 6 mils. The electrode width is again preferably designed at 0.012 inches, or 12 mils. In addition, it is with this unique type of electrode orientation that candidate sensor devices can be made smaller in terms of the overall width of the electrode pattern itself, thus enabling installation into significantly smaller access bores such as what might be found on the oil galley of a candidate diesel engine model.

FIG. 4 illustrates a planar-type sensor device with, in this particular example, three electrodes instead of two, as typically employed in classic electrochemical impedance-based measurements. Usually employed in other electrochemical techniques such as cyclic voltammetry, this three-electrode design performs equally as well as any of the other device designs mentioned hereto—that is, within the same embodiment of the impedance parameters described in connection with the invention. The line widths for this design are up to 20 mills, whereas the spaces can be patterned up to 20 mils just the same. Although readily apparent, it is the third electrode in this design—the reference electrode to be specific—that sets this device design apart from the others mentioned.

The surface area of any of these designs are intended to encompass somewhere on the order of one to four, square centimeters. Metallization layers such as gold- or silver-over-nickel are desirable where the respective understrike and overlay materials are each applied with a thickness of 100 microns and up to 25 or 50 microns, respectively. Moreover, it is important to note that, with any of these two- or three-electrode sensor designs, the electrical parameters are held constant in terms of the applied excitation stimulus comprised of the aforementioned DC bias, the applied voltage, and the sinusoidal frequency signal.

The electrochemical impedance between two electrodes is conventionally measured by imposing a voltage stimulus between the two electrodes and measuring the resultant current. The stimulus waveform is generally a sine wave at a designated frequency. The current that flows in response to this stimulus is often also a sine wave at the same frequency, but it is perhaps one which has been shifted a bit in time. The amplitude of the current and amount of its time (phase) shift may both be dependent upon the frequency chosen. Because a time-shifted (or phase-shifted) sine wave can be expressed as the sum of a sine wave and a cosine wave, we can write:

$$V(t) = V° \sin(\omega t)$$

$$I(t) = I° \sin(\omega t + \phi) = a \sin(\omega t) + b \cos(\omega t)$$

Where $$a^2 + b^2 = (I°)^2$$

$\omega$ is the frequency in radians/s $\phi$ is the phase shift in radians ($2\pi$ radians = 360° = one cycle)

In the equation for I(t), above, the sine coefficient, a, is referred to as the real or in-phase coefficient, or component, since it is 'in phase' with the voltage stimulus sine wave. The cosine coefficient, b, is referred to as the imaginary or out-of-phase component. The terms real and imaginary come from the mathematical construct of complex numbers.

The impedance (Z) expresses the relationship between V(t) and I(t) and also is referred to as having a real (in-phase) and imaginary (out-of-phase) component. In dealing with impedances, it is convenient to mathematically treat them as complex numbers. Impedance is the alternating current (AC), frequency dependent analog of DC resistance. The voltage can be found by multiplying the current by the resistance (DC) or by the impedance (AC). For DC, E=I R. By analogy, for AC, E=I Z, although E, I, and Z are treated as frequency dependent, complex numbers (i.e.—complex impedance).

For a simple resistor, the voltage and current are in-phase. For a capacitor, however, a sine wave voltage excitation produces a cosine wave current response. The current is 90° out of phase with the imposed voltage. The impedance of a resistor is treated as a real number (no imaginary part) while the impedance of a capacitor is treated as a purely imaginary complex number (no real part.)

Furthermore, the AC current that flows through a resistor does not depend upon the frequency of the imposed sine wave, while that which flows through a capacitor is inversely proportional to the frequency. The impedance of a resistor and that of a capacitor are given by:

For a resistor $$Z_{RESISTOR} = R + j(0)$$

For a capacitor $$Z_{CAPACITOR} = 0 - j(1/\omega C)$$

Where:
Z impedance
R resistance (ohm)
C capacitance (farad)
$\omega$ frequency in radians/sec
$j \sqrt{(-1)}$ Therefore, with the in-situ sensing device containing oil between its two closely parallel electrodes, the system can be divided into three parts: two metal-lubricant interfaces and the bulk lubricant layer. Under analysis, it is the corresponding electrical behavior of the bulk layer, and, it is postulated, the additional interfacial or electrochemical layers that form the basis of the impedance measurement described herein. Accordingly, the impedance response of the sensor can be best understood by modeling it with an equivalent circuit as shown in FIG. 5.

In this equivalent circuit, $R_{CT1}$ and $R_{CT2}$ represent the charge transfer resistance at electrodes 1 and 2, respectively. The charge transfer resistance at each electrode will depend upon the composition of the fluid with which it is in contact as well as the voltage between the two electrodes. $C_{DL1}$ and $C_{DL2}$ represent the double layer capacitance at electrodes 1 and 2. This capacitance may also depend upon the composition of the fluid that is in contact with the electrodes and, to a lesser extent, upon the voltage between the electrodes. $R_{oil}$ is the resistance of the bulk oil layer between the two electrodes.

It can thus be stated that the respective sensing device (dielectric lubricant along with said two identical electrodes) is represented, on a first order basis, by a resistor and capacitor pair that corresponds to the aforementioned bulk lubricant layer. It is the additional interfacial or electrochemical layers that, on a second order basis, represent the other resistor and capacitor pairs of said electrochemical impedance sensor. Collectively, then, it is the three respective subcircuits, or R-C couples, that can ultimately define the overall sensor response, with each resistor and capacitor pair connected in parallel for the equivalent circuit.

For a single R-C couple, the impedance data can be expressed in the form of a Bode plot that, as represented in FIGS. 6 and 7, is helpful toward characterizing the electrochemical impedance properties of the system. The Bode plot is constructed by plotting the logarithm of the magnitude of the impedance |Z| versus the logarithm of frequency (f), or the phase angle ($\theta$) between the AC potential and current.

At reasonable voltages between the electrodes (under 10 volts), electronic conduction (direct electron flow) through the oil is not significant. Movement of ions or charged species is the primary cause of electrical conduction. The value of the resistance depends upon the concentration of charged species in the oil matrix. These species may be deliberately added ionic additives. They may also be organic acids or salts formed from the oxidative breakdown of the oil, or inorganic acids or salts (sulfur- or nitrogen-based acids) introduced by contact with the products of the combustion of fuel. For a substance between two parallel plates, the resistance is proportional to the separation between the plates. In this case, the following can be expressed.

$$R_{oil} = \rho d/A = \rho/L$$

Where:
ρ resistivity of the medium
A area of plates
d separation between plates

For other geometries, an equivalent equation holds but with the ratio (d/A) replaced by (1/L), where L is a parameter which has units of length and depends upon the specific geometry of the sensor.

$C_{PHYS}$ is the physical capacitance of the sensor. $C_{PHYS}$ can be calculated from the geometry of the sensor and the dielectric constant of the material between them. This is given roughly by the equation for a parallel plate capacitor.

$$C_{PHYS} = \in \in_o A/d = \in \in_o L$$

Where:
∈ dielectric constant
$\in_o$ permittivity constant ($8.85 \times 10^{-12}$ farad/m)

Thus, the impedance of the sensor will be largely controlled by the oil resistance ($R_{oil}$) and physical capacitance of the sensor ($C_{PHYS}$) if the oil is not overly contaminated. The charge transfer resistances are expected to be large since the concentrations of electroactive compounds should be small. The double layer capacitances ($C_{DL}$) are expected to be on the order of μF by analogy with aqueous solutions. Under these conditions, the impedance of the sensor immersed in oil is dominated by the physical capacitance and the oil resistance. This is shown in the Bode plots of FIGS. 6 and 7. The circles and lines represent the sensor impedance while the squares and lines are the theoretical impedance calculated for a 300 pF capacitor ($C_{phys}$) in parallel with a 4.5 MΩ resistor ($R_{oil}$).

In previously conducted research efforts pertaining to the invention assignee hereto, impedance-based oil sensing methods were developed whereby the real part of the impedance was used to differentiate between fresh and progressively degraded oil conditions. In that work, the impedance was measured between two closely spaced wire electrodes at fairly high frequencies (with 300 kHz preferred) using a commercially available Hewlett Packard Impedance Analyzer. For the automotive and diesel locomotive engine oils tested, it was found that the real part of the impedance only changed (i.e.—decreased) by approximately a few percent over the useful life of the oil.

It is in accordance with the invention herein that related electrochemical impedance spectroscopy techniques are disclosed, but ones that produce considerably larger sensor output changes for the specific oil condition parameter being measured. These larger changes can thus be used to more reliably sense either the end of the useful service life of an oil under normal operations, or, as in the case of water and/or fuel, the occurrence of these contaminants due to problematic operating conditions.

In one embodiment of the current invention for monitoring oxidation levels in operational crankcase oils, a sinusoidal waveform at 1 V in amplitude is applied across a custom-fabricated, two-electrode sensor configuration to produce a frequency dependent current through the oil-electrode system. With electronic instrument means for producing a relatively low frequency AC signal connected to said electrodes, a frequency of less than 20 Hertz (Hz) is next chosen such that, for the specific cell constant at hand, the impedance measured is primarily composed of the real component of the complex impedance (although with much different results than said earlier high frequency methods).

It is another important element of the invention herein that the aforementioned Bode plot representation is used as the principal platform of analysis to precisely determine the specific oscillation frequency (and not a range) at which the overall sensitivity of said impedance measurement can be optimized. With reference again to FIG. 6, it is to this accord that, in practice, it is critical to note that the real component of the complex impedance dominates the impedance spectra on the horizontal, flat portion of the Bode |Z| plot. It should further be noted that, in a preferred practice of the respective Bode plot analysis platform disclosed herein, it is precisely a distinct frequency that corresponds to the respective horizontal or "real component plateau" of said Bode plot that should be selected to minimize the contribution of the imaginary component of the complex impedance. By selecting an oscillation frequency that's preferably an order of magnitude less than the transition frequency (i.e.—the "cusp" on the Bode curve in FIG. 6), such a measurement can assure that the real component of the overall impedance (resulting from the oil resistance) is the primary characteristic being measured.

Therefore, for certain crankcase oils, the oscillation frequency ranges between about 1 and 5 Hz, with approximately 1 Hz (or maybe less) being preferred. What is achieved at this distinct low frequency point is a robust sensing technique that, unlike higher frequency capacitance-type measurements, produces order-of-magnitude-level changes for new and end-of-useful-life engine oils.

There is an additional important aspect of the current invention for monitoring thermal-oxidative oil breakdown whereby, with said electronic instrument means, a DC bias potential is applied in addition to the aforementioned AC potential waveform. It has been found that, in practice, the application of a DC bias further refines the data acquired at the preferred distinct measurement frequency.

Therefore, as already noted above, it is from the applied voltage sine wave to the respective sensor, and resultant voltage and current responses collected by the instrument electronics, that said real components and imaginary components are used for what can be considered a single "complete" measurement. With the respective preferred algorithms stored in software, the ratios for these components can be calculated and thus the real impedance and imaginary impedance can be produced for the applied test frequency. This measurement and calculation together are given by the following equations:

$$E_{real}/I_{real} = Z_{real}$$

$$E_{img}/I_{img} = Z_{img}$$

From this relationship, it is of additional importance to note that resistive behavior of an electrochemical interface produces real impedance, while capacitive behavior produces imaginary impedance.

In addition, as another important element to the invention at hand, the degree of phase shift is calculated for the voltage and current responses at the applied frequency. This can be achieved from the following equation:

$$\text{Phase angle} = \text{Arctan}(Z_{img}/Z_{real})$$

With this calculation, the phase angle can be employed to determine the type of behavior the respective sensor device is experiencing at a given measurement frequency. Phase angle calculations close to zero (0) indicate resistive behavior (real impedance), while phase angles significantly greater than zero (0) indicate capacitive behavior (imaginary impedance). Therefore, it is at the chosen distinct frequency applied that the magnitude of the impedance consists primarily of the contribution from the real impedance component. And, with reference again to the Bode platform of analysis, this can be verified from the phase angle of 0° and the horizontal shape of the Bode magnitude plot at a chosen distinct frequency.

Thus, in terms of the overall sensor-driven output indication that is critical to the measurement at hand, the magnitude of the impedance |Z| is used (at a preferred low frequency) as the primary parameter, or "absolute indication," for differentiating between different brands and/or types of new engine oils and the degraded condition of same, once placed in service. It is thus critical to note that, for the impedance analysis method of this invention, the magnitude of the impedance |Z| is subsequently calculated according to the following equation:

$$|Z|=[(Z_{real})^2+(Z_{img})^2]^{0.5}$$

Operationally, as a candidate lubricant performs throughout its intended duty cycle, a subsequent increase or decrease is exhibited in the magnitude impedance |Z| that, over time, directly corresponds to the specific additive chemistry employed in the particular oil basestock to combat the thermal, oxidative, and other environmental stresses that lead to its breakdown. The respective sensor response, with accompanying algorithms and "intelligent" computer software on-board, can thus be used as a reliable, quantitative measurement of thermal-oxidative breakdown levels in crankcase oils still in service.

This important aspect of the in-situ sensing capabilities afforded by this impedance analysis technique is perhaps best illustrated in the form of a Nyquist plot. Illustrated in FIG. 8, the Nyquist plot is produced by plotting the imaginary impedance component against the real impedance component at each respective excitation frequency. In particular, it should also be noted that the diameter of a circular fit of the data is the aforementioned real component of the complex impedance. The circular data fits shown in FIG. 9 are indicative of Nyquist plots produced from the impedance analysis technique for fresh (baseline) and used oils of the same brand. Clearly, it can be seen that the fitted circle diameters correlate in a predictable & straightforward manner for each progressively-degraded oil sample tested.

Overall, then, it is in this precise manner for the respective two-electrode system, and for any other two-electrode sensor, that this impedance analysis technique can be controlled to significantly enhance the overall sensitivity, dynamic range, and resolution associated with the respective sensor output indication for thermal-oxidative oil breakdown. In addition, it is in this very context that the respective Bode plot analysis platform, from a pure electrochemistry standpoint, can afford precisely defined impedance measurements that produce the optimum response from a given device and medium, whether in crankcase oils or otherwise. In this case, the impedance analysis platform, by itself, can very nearly be construed as a pervasive, near-monolithic process for innovation in electrochemical sensor development.

The real and imaginary components of the impedance (or alternatively, the magnitude and phase of the impedance) can both be calculated, and continually monitored, to specifically characterize water contamination problems in operating machinery. The actual sensor response, however, depends upon the specific sensor structure employed for such contamination monitoring capabilities. In fact, it has been found that the specific sensor responses for planar-type versus parallel plate designs, or the aforementioned dual-wire-type devices, are markedly opposite one another. In accordance with FIG. 10, for instance, a substantial decrease in the magnitude impedance |Z| is detected (on a first order basis) with parallel plate structures and dual-wire-type devices (at room temperature) as water molecules come into contact with the oil-electrode interface. And, it is on a second order characterization basis that a distinct increase in the calculated phase angle of the complex impedance is illustrated in FIG. 11 for the closely parallel electrode structures. FIG. 12, on the other hand, clearly illustrates that, for this particular contamination experiment at 140° F., the magnitude impedance |Z| increases noticeably with the preferred planar-type devices. The calculated phase angle of the complex impedance, decreased itself by almost 67%. It is believed that the reason for these two markedly dissimilar responses, is due to the inherently unique external electric fields that are generated in the immediate vicinity of the respective electrode surfaces—each design resulting in a specific interaction with the combined water-hydrocarbon oil phase. Regardless of the specific sensor structure, however, the significant presence of water (>0.1%) in the oil (versus amounts from condensation) cannot only be detected, but simultaneously verified on a separate, distinct basis of impedance data analysis. In this case, the respective sensor responses for various water contamination phenomena (again with said "intelligent" algorithms embedded in software) can serve as a viable platform for negating potentially catastrophic engine failures due to such operational disparities.

Additional multiple discrete frequencies can be employed to gain more pervasive analytical capabilities for comprehensive oil condition monitoring. By implementing the equivalent circuit and Bode plot analysis steps just defined, continued impedance sensor testing will seek to define other unique combinations of: (1) voltage, (2) DC bias, (3) frequency, (4) amplitude modulation, and (5) novel data analysis techniques that can afford vital information on the other attendant oil parameter- or additive-specific measurements that are in wide practice in today's oil analysis laboratories (e.g.—TAN/TBN, FTIR, and/or DSC).

For instance, oscillation frequencies apart from those employed for degradation and water contamination monitoring can be employed to sense fuel dilution problems in operational engine oils. More specifically, it is proposed that relatively high oscillation frequencies between 20 Hz and 500 kHz can enable the specific characterization of several fuel-related contamination processes before they become excessive. Illustrated in FIG. 13, impedance measurements (although performed at the lower frequencies) have already shown considerable promise for producing, at a minimum, changes on the order of 18% for key fuel dilution levels at 2.5% and 5%, respectively. The results depicted in FIG. 13 for such real-time contamination monitoring capabilities were obtained on the basis of a simulated fuel dilution test whereby successive drops of heated fuel (up to 20 ml) were gradually introduced into 200 ml of heavily degraded, end-of-duty-cycle oil heated to 140° F.

Key information concerning the viscosity of an oil, and its changes, can be also gleaned from electrochemical impedance measurements performed over the warm-up stage of the candidate engine being monitored. From a data acquisition standpoint, it is anticipated that precisely timed (and stored) cold-start impedance measurements can afford critical data on the deterioration of the candidate oil's viscosity. With built-in temperature sensing, vital impedance data related to the changes in the temperature dependency of the oil under test can be precisely analyzed to achieve such important correlation capabilities.

Thus a theoretical model from which any given two-electrode system (regardless of cell constant) can be studied—again in terms of said equivalent circuit and Bode plot analysis platform—to establish the optimum measurement parameters for impedance output indication.

By observing both the real and imaginary components of the impedance, an indication of common sensor failure modes or other anomalies can be enabled. Specific failure modes or anomalies can include: (a) a break in the wires connecting the sensor to the instrument electronics package, (b) a sensor shorted by metallic wear particles, or (c) a sensor which is no longer immersed in oil.

Planar-type electrode pairs—either in parallel, interdigitated, or concentric configurations—can be employed to produce robust oil-condition-dependent responses from said electrochemical impedance analysis technique. As highlighted in FIGS. 1, 2, 3, and 4, for instance, there are at least several specific electrode configurations that, fabricated in a planar fashion, can each afford a desirable oil impedance output indication. It is in this context that, as described above, the ever-important Bode plot analysis platform should afford tangible proof that any claim of its near-monolithic application is warranted.

EXAMPLE I

As highlighted in FIG. 14, a bench-level test protocol was carried out over a wide range of oscillation frequencies to determine at what point on a Bode-type plot the greatest desirable change was produced in the magnitude impedance Z—that is, for two comparison oils. The three points of direct comparison shown in FIG. 14 were based upon electrochemical sensor data that was taken relative to a common fresh sample of Pennzoil 10W-30 automotive oil and a common used sample of the same stock—with each of the six output values derived from the same experiment. Very importantly, the data specified for the high and middle frequency range columns are representative of, in addition to U.S. Pat. No. 4,646,070 of Yasuhara, et al., said prior art in U.S. Pat. Nos. 4,733,556 and 5,540,086 as well as 5,274,335, respectively.

Given the three comparison oscillation frequencies, it can be seen that electroanalytical techniques in accordance with the current invention are far superior to others examined in the respective literature or in prior patent art. While low-frequency range measurements produced changes on the order of 275% for the candidate fluid at 3,900 miles of service, the competing high and mid-range frequency measurement techniques produced minimal changes between 6% and 13%. Thus, it is in this context that the aforementioned advantages cited with respect to enhanced sensitivity and expanded dynamic range are warranted.

EXAMPLE II

Electrochemical measurement and data analysis techniques in accordance with the present invention have been tested both at the bench-top level and on a fully operational internal combustion engine test-stand. Specifically, in-situ sensing capabilities have been tested & verified for the successful analysis of authentic fresh and used lubricating fluids, as well as laboratory-stressed crankcase oils. The candidate oil formulations that have been studied for determining quantitative levels of oil degradation, water contamination, and fuel dilution include: (1) locomotive diesel engine fluids, (2) automotive crankcase oils, and (3) heavy-duty, diesel truck engine oils. Importantly, for all of the vocation-specific oils that have been examined for desired oil degradation and contamination monitoring capabilities, it has been empirically documented that electrochemical measurement and data analysis techniques in accordance with the invention herein are highly sensitive to even subtle changes in oil quality. For instance, as indicated in FIG. 15, a fresh sample, a degraded sample, and a series of blended samples have been tested in accordance with the low frequency impedance measurement techniques described herein. It should be noted for the blended samples that—for any of the seven blended samples between 10% and 85%—each one was blended at a ratio that was always, in effect, at an equilibrium 120-ml quantity. In this way, on a full 100% scale for oil degradation, each sample represented a scientifically correct comparison point for the respective blend level indicated. What was intended to be produced by the respective blending technique was a complete sample set of oils that were "tightly grouped" in terms of a progressive level of oil degradation up to a point of 4,692 miles service where the oil would likely represent a completely broken down fluid. Therefore, as the respective sensor responses are listed for each sample studied, it was empirically verified that relatively small variations in oil quality could easily be detected by the low frequency impedance measurements of the current invention. Moreover, this is the fundamental basis upon which the aforementioned claims concerning enhanced resolution features were made. The produced sensor responses also exhibited a desired degree of linearity when plotted graphically. Quite importantly, this is indicated in FIG. 15 where, for each of the data points up to the H3D20 sample, the data represents an approximate 600% change in the sensor output for our simulated 4,692-mile duty cycle.

It was further pointed out above that three-electrode-type configurations can be employed just the same to produce the desired output impedance indication.

EXAMPLE III

In order to study the electrochemical behavior of the two-electrode sensing devices over long-term applications of in-situ analysis, a custom-built test apparatus has been employed to stress engine oils in the laboratory. What was intended to be achieved with this unique bench-top apparatus was a highly controllable experiment that would closely parallel the physical and chemical phenomena encountered in operational, in-service engine conditions. Specifically, an overbased Ethyl-brand of railroad oil was stressed continuously over a 120-hour period by introducing oxygen at a rate of 5.0 L per hour through a sparge tube positioned below the surface of 1.2 L of oil sample maintained at 320° F. The respective oxidation cell further contained iron, copper, and lead coupons (1"×1" square pieces) to serve as oxidation catalysts and simulate the metallurgical conditions of an internal combustion engine. As such, the physical and chemical breakdown of the test oil could then be monitored in real-time from a sensor immersed in the test lubricant over the entire 120-hour test sequence.

As indicated in FIG. 17, the 120-hour in-situ test at 320° F. resulted in a highly straightforward, logarithmic-type plot for the candidate oil's oxidation stability. It was further empirically verified that in-situ sensing devices in accordance with the present invention could not only produce a desirable degree of sensitivity and resolution, but an overall level of stability and/or predictability for successfully monitoring crankcase oils in extreme conditions of thermal-oxidative breakdown. It should also be noted that the respective graph in FIG. 17 demonstrates a favorable degree of correlation with specific analytical parameters utilized by the trucking and rail industries for determining an oils operational acceptance or condemnation.

In FIG. 18, for instance, laboratory measurements for Total Base Number (TBN) are presented for the aforementioned laboratory-stressed diesel locomotive oil. Plotted graphically, the original TBN for the candidate oil was 17; however, the subsequent laboratory analyses performed for TBN indicate values of 3.91, 1.47, 1.28, 1.16, and 0.85 at 12, 36, 60, 84, and 108 test hours, respectively. Very importantly, the comparison of FIGS. 21 and 22 indicates that the present invention produces electronic signals (MOhms in this case) which provide a correlation to the physical and chemical breakdown of said engine oil and may be employed in an on-board system to enable an early warning of conditions warranting that the oil should be changed.

EXAMPLE IV

In-situ test trials of the electrochemical measurement and data analysis techniques for water contamination have also proven successful with regards to several key contamination levels and a single critical threshold value for water as well—that is, evaluation criteria exactly specified by OEMs such as General Electric's Locomotive Division. It is toward this end that FIG. 19 is presented wherein real-time experiments were conducted to determine the potential water detection limits of said electrochemical, two-electrode sensor device.

With regard to the aforementioned critical contamination level, it was from this experiment that two (2) substantial drops in sensor output were seen for just three (3) 0.025 ml drops that were added to a vigorously stirred, 200 ml sample of degraded oil at 2,200 miles service. The arrows, as placed, are intended to indicate the separate points at which each of the three (3) drops of water (that is, a level of 0.075%) were added to our test oil. Granted, there is a slight delay between the introduction of water and a noticeable sensor response, yet this is undoubtedly due to the time required to fully disperse the water in the oil. More important, however, as evidenced in this experiment, it can be clearly seen that the respective sensor device and impedance measurement technique are capable of detecting less than the 0.075% water that was introduced into the degraded oil sample. In fact, the initial sharp drop in sensor output at 10 minutes (say from roughly 590 to 108) is probably the response to the first or second drop added (that is, 0.025% or 0.05% water); while the drop at 14 minutes (from around 190 to 12) most likely represents the dispersal of the second or third drop (that is, 0.05% or 0.075% water). Finally, what was produced from the respective experiment (and, in this case, displayed in real time) was a dual 482- and 178-point change for a gradual assimilation of water into our test cell—all over an approximate 10-minute period of real-time data acquisition.

EXAMPLE V

In accordance with FIG. 20, there is depicted in schematic form an embodiment of the in-situ, on-line oil condition monitoring system 10 used to generate the above-described oil-condition-dependent output indication |Z|. System 10 includes a removable potentiostat module 12 installed within an oil pan wall 14 of an internal combustion engine oil reservoir. The removable potentiostat module 12 includes a metal housing 16 that preferably includes an intermediate threaded section 18 that is precisely machined to correspond to the existing threaded bore 20 of the oil pan wall 14. On the end of the metal housing 16 there is found semi-permanently connected to distal threaded portion 22 the replaceable sensor assembly 24. As the intermediate threaded section 18 is screwed into threaded bore 20, replaceable sensor assembly 24 extends into the engine crankcase where it is exposed to the lubricating oil 26 therein. A circular O-ring 28, made of a material such as silicone, may also be positioned between the metal housing 16 and the oil pan wall 14, as shown in FIG. 20.

The preferred plastic shell portion 30 serves as an enclosure to the electronic components that comprise the removable potentiostat module 12. Plastic shell portion 30 further includes an ergonomically-shaped exterior surface along the 2—2 line of FIG. 20 which permits a maintenance technician, mechanic, or equipment owner, etc. to thread the removable potentiostat module 12 into or out of the existing threaded bore 20 as desired by direct hand tightening means. Mechanical structures such as wrench flats are also contemplated as desired for facilitating the installation or removal of the removable potentiostat module 12 from the existing threaded bore 20 of the oil pan wall 14.

Again referring to FIG. 20, there is shown, extending outward from the preferred plastic shell portion 30, a preferred 90° header-style connector 32 permanently connected to potentiostat device circuitry 34. Referenced by line 3—3 in FIG. 20, there is further illustrated the cable harness assembly 36 that, with shielded, 12-conductor cable 38 appropriately matched in between, is comprised of connector and sealed female mating plug pairs 32, 40 and 42, 44, respectively, at each end. In the preferred embodiment, the shielded cable 38 is less than 10 feet in length, but may be up to 50 feet, as necessary, for installation of said oil condition monitoring system in such equipment platforms as diesel locomotives. It is with the cable harness assembly 36 that the output signal of the below-described instrument electronics package 46 is conducted to the potentiostat device circuitry 34 whereby, prior to an actual measurement, the signal is preferably buffered, or conditioned, via preferred electronic means. Once conditioned, the respective output signal then conducts to the replaceable sensor assembly 24 via the electrical interconnect component 48 to produce an oil-condition-dependent response to the below-described stimulus voltage provided by the instrument electronics package 46. The resultant impedance-based sensor response, again passing through another contact of electrical interconnect component 48, is next conducted back to the potentiostat device circuitry 34 where again the return signal is conditioned to be electrically transmitted through, in this case, another conductor in the cable harness assembly 36. At this point, the below-described instrument electronics package 46 processes the respective analog signals from replaceable sensor assembly 24 to produce a meaningful output indication |Z| for said operational lubricating oil medium 26.

Figure 21:
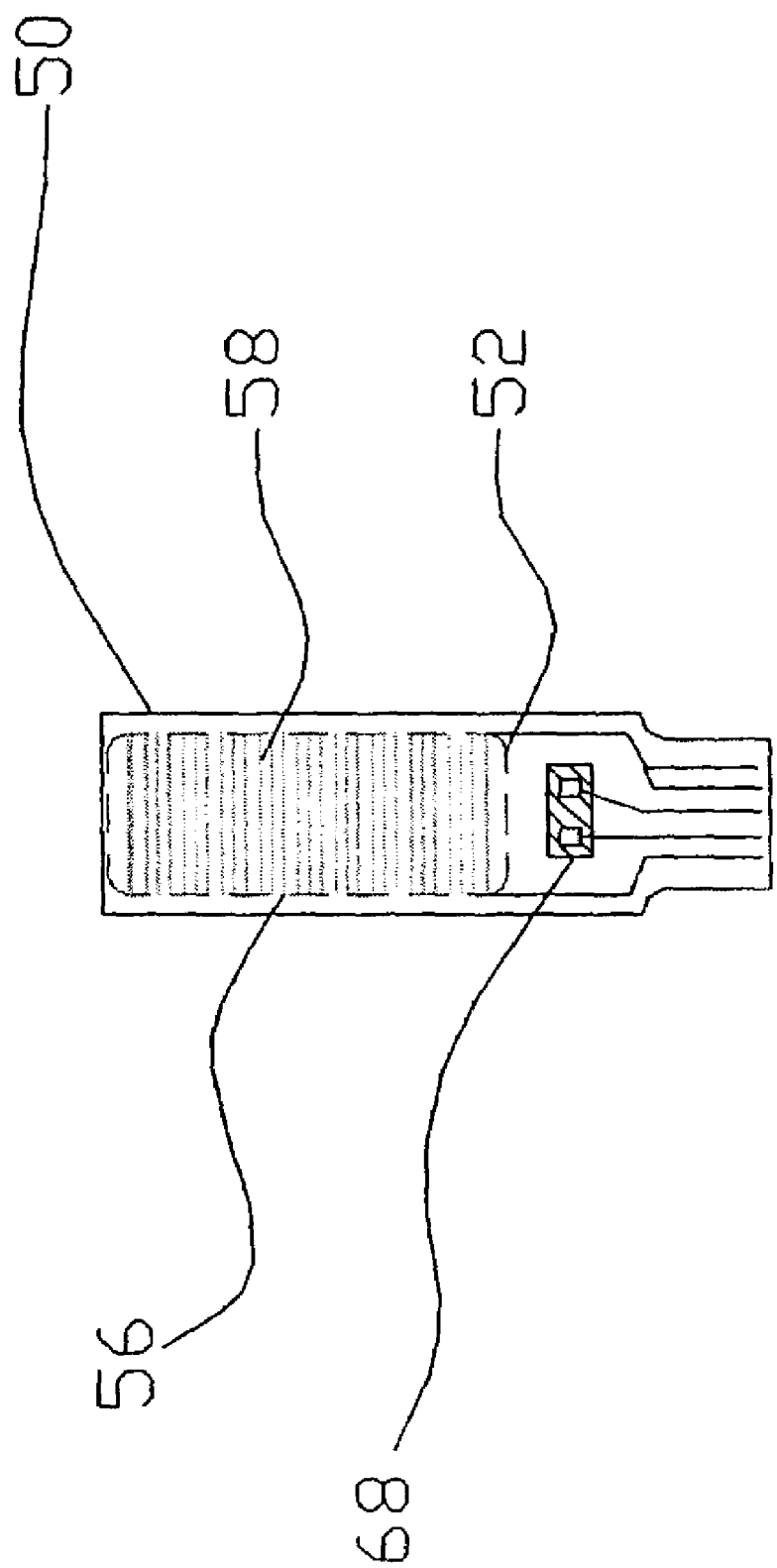
FIG. 21 illustrates in schematic form an interdigitated planar-type oil sensing device of the present invention.

As shown in FIG. 21, the primary sensor substrate 50 serves as the base layer (or component) upon which unique electrode array configurations can be produced. It is from the individual electrodes that lie in the sensor array opening 52 that the oil-condition-dependent output indication |Z| is generated. The primary sensor substrate 50 is preferably manufactured from a low-cost, yet thermally stable material which readily lends itself to standard wet chemical etching processes for creating specific electrode geometries. For example, the primary sensor substrate 50 may be fabricated from standard FR-4 material. It is further contemplated that a ceramic material such as alumina could also be used. As described above, FIG. 20 further illustrates that the electrode configuration 58 is preferably produced in an interdigitated (IDT) configuration wherein the respective two (2) closely parallel electrodes have a gap between them of just less than or equal to about 150 microns, or 0.15 mm. It is also preferred that the counter and working electrodes 72 and 74, respectively, are fabricated to have a thickness of between 0.006 and 0.012 inches, or 6 and 12 mils. Also in the preferred embodiment of the invention hereto, the surface area 56 is produced to encompass somewhere on the order of one to three square centimeters. Metallization layers such as gold- or silver-over-nickel are also preferred where the respective understrike and overlay materials are each applied with a thickness of 100 microns and up to 25 or 50 microns, respectively.

Figure 22:
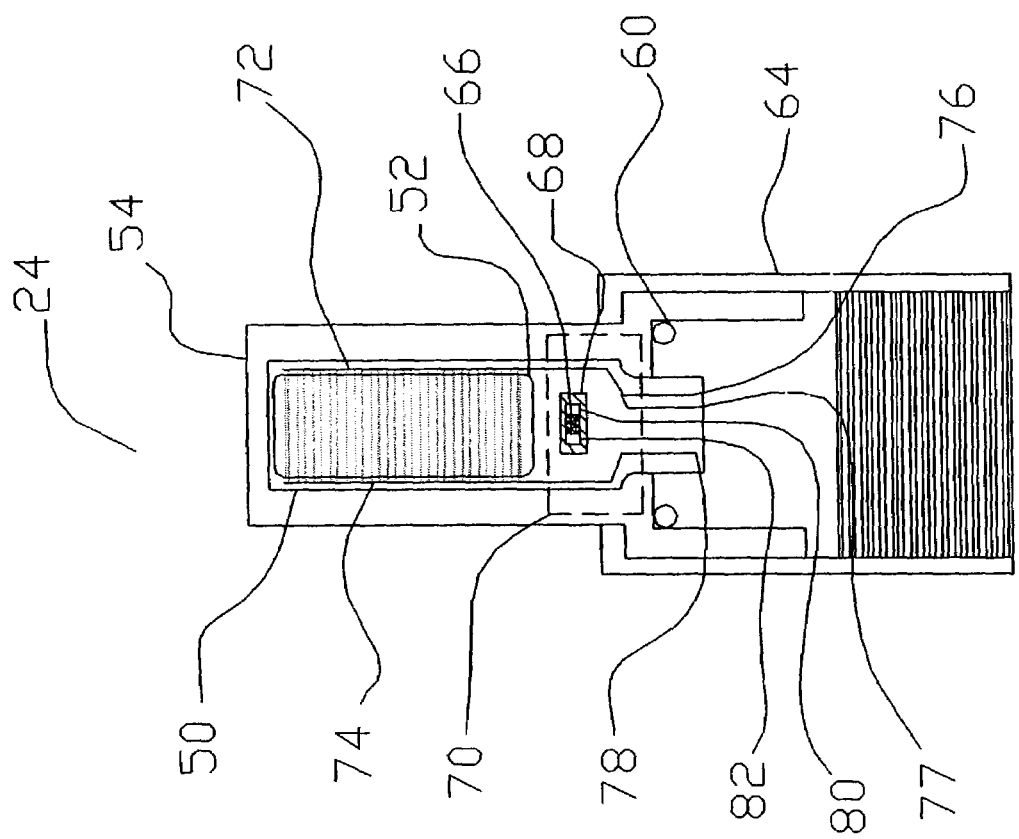
FIG. 22 is a top view partly in section of the replaceable sensor assembly of the present invention.
Figure 23:
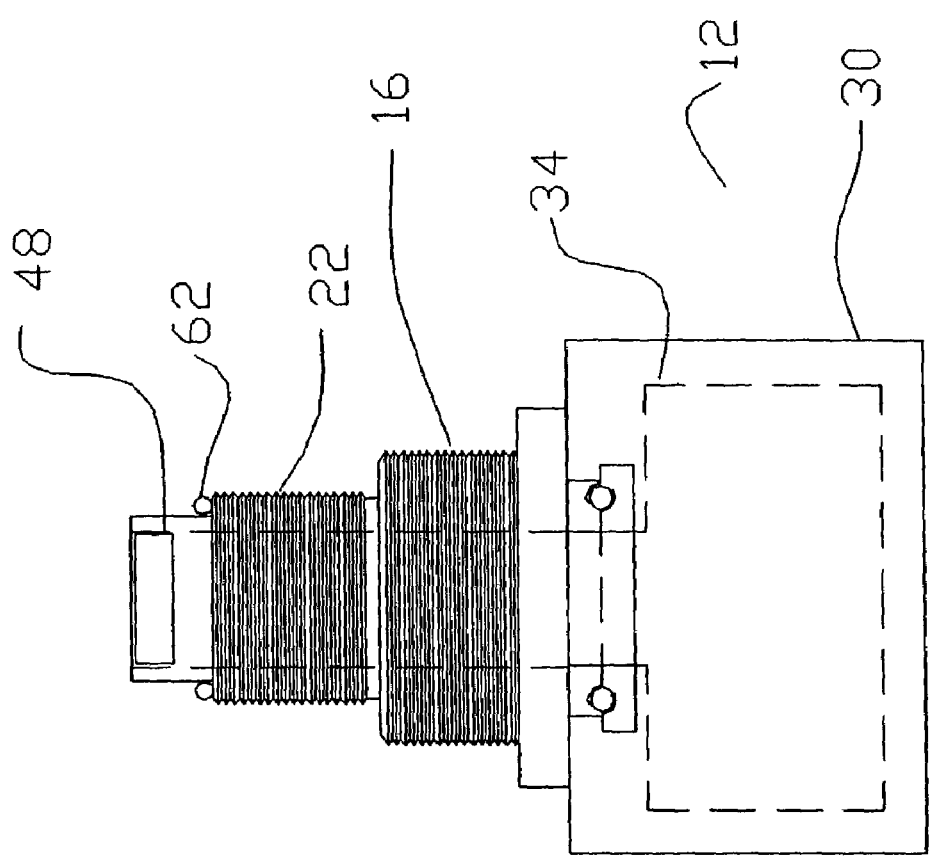
FIG. 23 is a top view partly in section of the removable potentiostat module of the present invention.

Referring to FIG. 22, the replaceable sensor assembly 24 includes a plastic housing 54 (manufactured from an engineering-grade thermoplastic) which is actually in direct contact with the hot lubricating oil medium 26. The plastic housing 54, and particularly the sensor array opening 52, are precisely machined to receive the primary sensor substrate 50. The sensor array opening 52 is preferably sized to form a rectangular-shaped recess, or window, along the length of a candidate sensor array etched on the primary sensor substrate 50. Accordingly, the primary sensor substrate 50 is preferably rectangular in shape and the surface area 56 of the respective electrode configuration 58 is precisely defined such that it is slightly greater than the perimeter of said window comprising sensor array opening 52. It is in this preferred embodiment that, in conjunction with hard plating electrode fabrication methods, the precise dimensioning of both the sensor array opening 52 the surface area 56 helps to mechanically ensure the respective electrode configuration 58 will avoid peeling up while in the hot lubricating oil medium 26. To create an oil-tight (i.e.—leak proof) seal, as shown in FIGS. 22 and 23, the silicone O-rings 60 and 62 are employed whereby, in a preferred embodiment of the invention, the threaded jam nut 64 is precisely machined to screw directly onto the distal threaded portion 22 of the metal housing 16. It is with the preferred jam nut 64 that, upon tightening, the silicone O-rings 60 and 62 are forced into a state of compression, thus affording a highly-reliable, leak-proof design.

Again referring to FIGS. 21 and 22, the replaceable sensor assembly 24 further includes other electronic components and supporting circuitry that resides internal to said assembly. For instance, the replaceable sensor assembly 24 preferably includes a temperature sensitive resistor 66 (i.e.—thermistor component) which is mechanically and electrically attached to the thermistor contact area 68 of the primary sensor substrate 50 by a standard SMT (surface mount technology) production process. Embedded within the inner cavity 70 of the plastic housing 54, and preferably isolated from the electrode configuration 58, the temperature sensitive resistor 66 provides a reliable voltage output for determining the temperature of the lubricating oil medium 26 via the thermal transfer properties of the plastic housing 54.

In accordance with FIG. 23, there is depicted partly in section a top view of the removable potentiostat module 12. The removable potentiostat module 12 includes circuitry that resides in both the metal housing 16 and plastic shell portion 30 for generating the oil-condition-dependent output indication |Z| from, as shown in FIG. 22, the replaceable sensor assembly 24 that tightens onto the distal threaded portion 22 shown again in FIG. 23. The critical electrical circuit elements of the removable potentiostat module 12 are preferably implemented in accordance with potentiostat device circuitry 34 which, as previously touched upon above, is in electrical contact with the respective electrode configuration 58 and temperature sensitive resistor 66 via electrical interconnect component 48.

More specifically, with reference again to FIGS. 22 and 23, the counter and working electrodes 72 and 74 that reside in the sensor array area 52 are electrically connected to potentiostat device circuitry 34 by traces (lead pairs) 76 and 78, respectively. And, it is with traces 80 and 82 that the temperature sensitive resistor 66 is also in direct electrical connection with the potentiostat device circuitry 34. It should further be noted from FIGS. 22 and 23 that the leads 76–82 of primary sensor substrate 50 are preferably connected to a plurality of contacts that readily enable the replaceable sensor assembly 24 to be easily attached and subsequently removed from the removable potentiostat module 12. As just specified above, it is the electrical interconnect component 48 that is preferably employed in support of this objective to both mechanically and electrically connect traces 76–82 to the critical circuit elements of potentiostat device circuitry 34. The electrical interconnect component 48 further includes means for enabling multiple cycles of engagement and disengagement with respect to the replaceable sensor assembly 24. For example, dual rows of multiple contacts are preferably employed with gold-over-nickel plating material. It is in accordance with this preferred embodiment of the invention that the electrical interconnect component 48 readily enables the replaceable sensor assembly 24 to be replaced, as is recommended, with every oil change that is performed over an extended period of engine operating time. In addition, the insulating package, or housing, that encloses the said multiple contacts should preferably be made of a high-temperature thermoplastic material to withstand the hot lubricating oil medium 26 in contact with the metal housing 16 installed in the threaded bore 20 of the oil pan wall 14.

Figure 24:
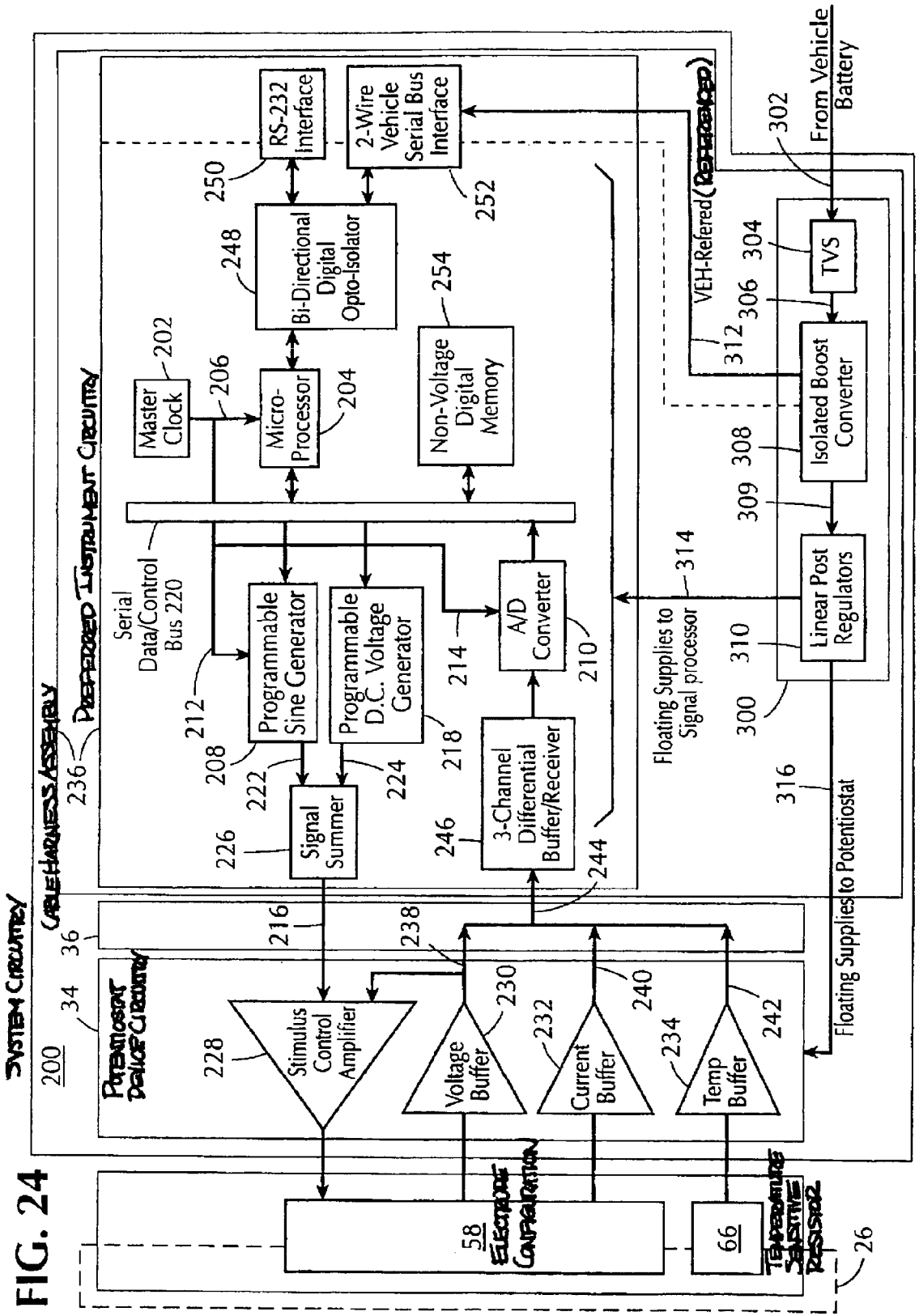
FIG. 24 illustrates in block diagram form the preferred system circuitry of the present invention.

In accordance with FIG. 24, there is illustrated in block diagram form the preferred system circuitry 200 of the on-line oil condition monitoring system 10 used to generate the above-described oil-condition-dependent output indication |Z|. The function of the preferred system circuitry 200 is to provide all the necessary signal inputs, outputs, and processing necessary for a stimulus response measurement. Timing and synchronization for all of the following below-described functions are provided by the master clock 202. The master clock 202 provides high frequency pulses to microprocessor 204 via line 206 to properly synchronize said component in a number of control operations, all as described below. The master clock 202 also provides high frequency pulses to programmable sine generator 208 and A/D converter 210, via lines 212 and 214, respectively, to properly synchronize the respective components in their required functions as well.

First, for the stimulus on line 216, it is composed of a programmable DC voltage and a programmable AC voltage, with the AC portion capable of being adjusted in both frequency and amplitude. Providing the respective stimulus are the programmable sine generator 208 and the programmable D.C. voltage generator 218, with each said component receiving its programming from the microprocessor 204 via the serial data control bus 220 on lines 222 and 224. The frequency of the AC portion, it is preferred, is some rational fraction of the master clock 202. The two signals on lines 222 and 224 are added together via signal summer 226 and provided as a stimulus on line 216 to the potentiostat device circuitry 34 via cable harness assembly 36.

Referring now to FIGS. 22–24, the potentiostat device circuitry 34 is used to control the sample (i.e.—the portion of lubricating oil 26 directly in contact with the electrode configuration 58) so as to instantaneously maintain a difference in potential E between the counter electrode 72 and the working electrode 74. It is further preferred that, simultaneously with any on-line measurement, the said potential difference is equal to the summed stimulus signal on line 216 of the preferred system circuitry 200. In operation, the counter electrode 72, which optionally can be connected to the reference electrode 77, provides electrical drive current (i.e.—a stimulus voltage) from line 216 to the lubricating oil medium 26 in contact with the respective electrode configuration 58.

The respective stimulus voltage transmitted from signal summer 226 to electrode configuration 58 is a sinusoidal waveform at 1V in amplitude to produce a frequency dependent current through the lubricating oil 26. In addition, with the microprocessor-controlled instrument circuitry 236, the excitation frequency on line 216 is selected such that, at less than 100 Hz, the impedance measured is primarily composed of the real component of the complex impedance.

In addition to the stimulus voltage applied to the counter electrode 72, a DC bias potential is also applied to said electrode on line 216 of the potentiostat device circuitry 34 from the programmable DC voltage generator 218. As discussed above, this technique results in the overall refinement of the data produced at the preferred distinct measurement frequency.

With these measurement parameters applied to the sample, the stimulus control amplifier 228 reproduces the signal on line 216 at the counter electrode 72, all precisely in accordance with the electrical feedback signals being monitored and returned by the voltage buffer 230 of the potentiostat device circuitry 34. The current portion of the stimulus response measurement, again as shown in FIG. 24, is transformed into a buffered voltage by the current buffer 232.

Also shown in FIG. 24, the potentiostat device circuitry 34 further includes other circuit elements for automatic correction of the output indication |Z| due to the effects of changes in the temperature of lubricating oil medium 26. Electrically connected with temperature sensitive resistor 66, temperature buffer 234, for instance, is employed whereby the voltage output of the resistor 66 is current biased, and buffered.

Collectively, then, there are three (3) critical responses obtained via the potentiostat device circuitry 34 from the replaceable sensor assembly 24 in the lubricating oil medium 26. The specific voltage inputs provided to the below-described instrument circuitry 236 for subsequent processing and analysis are as follows: First, as shown on line 238, the resulting difference in the potential (E) measured between the counter electrode 72 and working electrode 74 is converted into the single voltage (E)out. Second, as shown on line 240, the resulting current (I) flowing in the working electrode 74 is converted into the voltage (I)out. Third, as shown on line 242, there are the respective voltages produced from the temperature sensitive resistor 66 and the associated temperature buffer 234—voltages that, in practice, represent the non-linearized temperature of lubricating oil medium 26. The three (3) respective analog signals transmit along line 244 of the cable harness assembly 36 and are supplied to the three-channel, differential buffer receiver circuit 246 that, at this point, provides said signals as inputs to A/D converter 210. These converted signals are next provided to the microprocessor 204 via the serial data control bus 220 for subsequent processing and analysis, or correction. The update rate for A/D converter 210, it is also preferred, is programmed to be a rational multiple of the AC stimulus frequency on line 216.

With the complex impedance already discussed in extensive detail above, the converted single voltages for the (E) and (I) data streams on line 244 are converted into an impedance vector by the microprocessor 204. The ratios for the respective single voltage and current values are first calculated by the microprocessor 204 to record both the real impedance and imaginary impedance from said applied test frequency on line 216. This particular measurement and calculation together are given by the following equations:

$$E_{real}/I_{real} = Z_{real}$$

$$E_{img}/I_{img} = Z_{img}$$

It is another important preferred element to the invention at hand that the degree of phase shift is calculated by the microprocessor 204 for voltage and current responses recorded. This can be achieved from the following equation:

$$\text{Phase angle} = \text{Arctan}(Z_{img}/Z_{real})$$

Recorded values from this equation are used to first verify phase angle calculations close to zero (0), and thus resistive behavior at the electrode configuration 58 (real impedance). Thus, in terms of the primary measurement feature of the on-line oil condition monitoring system 10, the sensor-driven impedance output indication |Z| for the operational oil medium 26 is defined by the following equation:

$$|Z| = [(Z_{real})^2 + (Z_{img})^2]^{0.5}$$

It is with this algorithm stored in the microprocessor 204 that, still referring to FIG. 24, the produced calculation for the impedance |Z| is used to characterize and differentiate between different brands and/or types of new engine oils and, once placed in service, the degraded condition of same.

As the lubricating oil medium 26 begins to break down (oil degradation), the respective impedance output indication |Z| from the microprocessor 204 increases or decreases as a function of the specific additive chemistry employed in the particular oil basestock to combat the thermal, oxidative, and other environmental stresses that lead to its breakdown.

The real and imaginary components of the impedance (or alternatively, the magnitude and phase of the impedance) can be continually recorded by the microprocessor 204 to specifically characterize water contamination problems in problematic engine systems.

At the same time, the respective magnitude and phase of the impedance |Z| is continually monitored by the microprocessor 204 in order to detect and directly characterize fuel contamination problems occurring in the oil medium 26.

Referring to FIG. 24, the digitized voltage of the temperature buffer 234 is used to normalize the on-line, instantaneously-calculated impedance |Z| to a standardized operating temperature for the lubricating oil 26.

The microprocessor 204 of the instrument circuitry 236 further enables an automatic calibration of the on-line oil condition monitoring system 10. It is upon the occurrence of a performed oil change, for instance, that the microprocessor 204 engages itself to produce a baseline impedance output indication |Z| for the candidate brand of lubricating oil 26 being added to an engine's crankcase. And, from an applications standpoint, such self-calibrating capabilities readily facilitate direct application across a wide variety of different oil formulations and brands of lubricants such as in the case of: (1) Diesel/Gas Engines, (2) Gas Turbines, (3) Transmission Fluids, and (4) Hydraulic Fluids. The embedded memory associated with the microprocessor 204 can, in this manner, be used to store baseline information pertaining to a wide array of different additive chemistries, thus not only enabling widespread use, but further identification of improper motor oils (i.e.—via a markedly out of range impedance indication) being added to a candidate lubricating oil reservoir.

As already highlighted above, the microprocessor 204 also enables an automatic detection and indication of common sensor failure modes, or other anomalies. First, referring again to FIG. 24, the measurement and recording of the real and imaginary components of the magnitude impedance |Z| is employed via microprocessor 204 to determine and subsequently indicate a failure in the cable harness assembly 36 via the cessation of current through the electrode configuration 58. Second, the measurement and recording of the real and imaginary components of the magnitude impedance |Z| is employed via microprocessor 204 to also determine and subsequently indicate a problematic condition with the replaceable sensor assembly 24 whereby a noticeably low impedance value would be recorded due to the electrode configuration 58 becoming shorted by metallic wear particles in the oil medium 26. Third, the measurement and recording of the real and imaginary components of the magnitude impedance |Z| is further employed via microprocessor 204 to determine and subsequently indicate the replaceable sensor assembly 24 is no longer immersed in the oil medium 26 whereby the recorded impedance |Z| is no longer dominantly resistive.

Again referring to FIG. 24, the bi-directional digital opto-isolator 248 preserves the galvanic opto-isolation between the microprocessor 240, RS-232 interface 250, and SAE/TMC J1708/J1587 standard vehicle bus 252. Overall, the microprocessor 204 performs the following functions: (1) initializes and programs the AC and DC generators 208 and 218, respectively, (2) initializes and programs the A/D converter 210, (3) performs necessary processing and analysis of both the voltage (E) and current (I) data streams coming from the A/D converter 210, (4) linearizes the output of the temperature sensitive resistor 66, (5) calculates the output indication |Z| of the lubricating oil medium 26 from said processing and analysis of voltage (E) and current (I) data streams, (6) corrects said output indication |Z| calculated as a function of the measured oil temperature in accordance with a proprietary algorithm in software, (7) stores and/or logs data in non-volatile memory 254 via serial data control bus 220, (8) provides an operator interface via the industry-standard RS-232 architecture 250, and (9) provides a direct interface to the SAE/TMC J1708/J1587 standard vehicle bus 252 for a bidirectional, serial communications link between existing truck components.

While still referring FIG. 24, there is shown the power supply electronics 300 that provides regulated power to the instrument circuitry 236. For simplification, the operating supply voltage and a ground are generally shown as being provided to power supply electronics 300 via the vehicle power bus 302 (12 V–24 V nominal). This is achieved via a two-conductor, 18–22 AWG wire harness assembly permanently connected to the existing 12–24 V supply of the candidate piece of equipment, machinery, or other engine platform in which the instrument circuitry 236 is being permanently installed. The power supply electronics 300 consists of galvanically-isolated, or floating, power supply circuitry for both the instrument circuitry 236 and the potentiostat device circuitry 34, as well as vehicle ground-referenced power for the RS-232 interface 250 and SAE/TMC J1708/J1587 standard vehicle bus 252. Power supply electronics 300 is composed of a transient voltage suppression/over-voltage protection circuit 304 (as described in SAE J1455) feeding a regulated, multiple-output, transformer-isolated, boost-mode switching converter 308 via conditioned power bus 306. In addition, power supply electronics 300 is designed whereby the boost converter outputs 309 are separately post-regulated with linear regulators to produce the following outputs: (1) floating +/−2.5 V for the potentiostat device circuitry 34, (2) floating +8.0 V for the microprocessor 204 (with its internal regulator), (3) vehicle-grounded +5.0 V for digital interface circuits 250 and 252 which cross the floating isolation barrier, and (4) floating +3.3 V and +/−5.0 V for all remaining circuitry. More detailed descriptions of such power supply devices are readily available to those skilled in the art and therefore are not supplied herein. In an embodiment of the invention the input power transient handling and galvanic isolation noise characteristics are optimized for automotive systems.

While the methods, systems, and specific apparatus described herein constitute embodiments of this invention, it is to be understood that the preceding detailed description and accompanying drawings illustrate the principles of the invention. The invention is not limited to either the precise method or system apparatus disclosed herein. Various changes and modifications may be made thereto without departing from the scope of the invention. Thus, by way of example and not of limitation, other materials such as alumina oxide and/or silicon could also be used as viable substrates for the electrode configuration 58. It is further contemplated that the two-electrode configuration 58 could be designed in either parallel-plate-like or dual-wire-type device structures without departing from the scope of the invention. In addition, electrical changes could also be carried out in terms of different features that might be employed to further augment the preferred system apparatus disclosed herein. A conventional momentary contact reset switch, for example, could be added to the preferred instrument circuitry 236.

Separate or stand-alone display units could further be added to said system apparatus whereby such devices might include: (1) a bar-type, continuous LED readout, (2) a numerical liquid crystal display, and (3) other advanced digital computing/display devices in widespread use for mobile applications. At the same time, mechanical changes could also be made to the system apparatus disclosed herein. For instance, in the case of a candidate engine with only a single drain port, the metal housing 16 of the removable potentiostat module 12 could be designed to be mounted in the drain port of the oil reservoir whereby such a device would entail both an opening and closure means for draining and subsequently refilling the engine crankcase with motor oil.

Inherently, in-situ-type electrochemical impedance techniques and/or sensor systems for real-time oil condition monitoring can afford widespread use-value across a variety of different engine, transmission, hydraulic, compressor, and pump platforms. Accordingly, any transference of the impedance techniques, or associated apparatus described herein, to other various lubricating fluids and/or equipment/ engine platforms will still be considered within the scope of this invention. In closing, additional mechanical and electrical changes of a comparable nature could also be made.

Accordingly, the invention hereto is not limited to the specific methods, systems, or apparatus described in detail and illustrated by the schematics/diagrams hereinabove.

What is claimed is:

1. A method for optimizing the electrochemical measurement parameters of an impedance analysis technique for analyzing lubricants for thermal-oxidative breakdown, water contamination, or fuel dilution, or combinations thereof, comprising the steps of:

bringing electrodes into contact with a sample of oil;

applying a direct current (DC) voltage bias to one of said electrodes;

applying an electrical potential to the sample to produce an electrical current therethrough;

applying a frequency variation as a sinusoidal frequency stimulus (f) of a first value to the sample to produce a frequency-dependent current response (I) therethrough;

varying said sinusoidal frequency stimulus (f) to the sample from the first value to a second value and continuing said frequency variation to a third and successive additional values to produce a frequency-dependent current response (I) therethrough;

measuring and recording a voltage response (E) from said electrical potential and sinusoidal frequency stimulus (f);

measuring and recording the frequency-dependent current response (I) during said frequency variation steps;

recording from said voltage response (E) and said frequency-dependent current response (I) the ratio of the real component (E) versus the real component (I) of said impedance analysis technique over frequency (f);

recording from said voltage response (E) and said frequency-dependent current response (I) the ratio of the imaginary component (E) versus the imaginary component (I) of said impedance analysis technique over frequency (f);

computing the sum of the square of said ratio of real component (E) versus real component (I) and said ratio of imaginary component (E) and imaginary component (I) all to the one-half power;

recording the magnitude of the impedance |Z| from said sum of the square of the ratio of real component (E) versus real component (I) and the ratio of imaginary component (E) and imaginary component (I) all to the one-half power;

recording the logarithm of said magnitude of the impedance |Z| versus the logarithm of frequency (f);

recording the phase angle (θ) between the voltage response (E) and said frequency-dependent current response (I) versus the logarithm of frequency (f);

determining from said logarithm of the magnitude of the impedance |Z| versus the logarithm of frequency (f) the point of transition from a frequency-dependent impedance response to a frequency-independent impedance response;

identifying a stimulus frequency from the recorded logarithm of the magnitude of the impedance |Z| versus the logarithm of frequency (f) that is at least one order of magnitude less than said point of transition from said frequency-dependent impedance response to said frequency-independent impedance response;

verifying from said recording of the logarithm of the magnitude of the impedance |Z| versus the logarithm of frequency (f) that the shape of said frequency-independent impedance response is of a horizontal nature;

verifying from said recording of the phase angle (θ) that said phase angle (θ) is close to 0° versus the frequency-independent impedance response recorded;

analyzing the recorded frequency-independent impedance responses for said magnitude of the impedance |Z| and said phase angle (θ) to directly characterize said thermal-oxidative breakdown, water contamination, or fuel dilution conditions in said sample of oil;

comparing said frequency-independent magnitude of the impedance |Z| and phase angle (θ) values with predetermined values corresponding to said characterized sample conditions; and determining the quality and/or condition of the sample of oil as a function of the comparison.

2. The method of claim 1 wherein the DC voltage bias is 3.0 V or less.

3. The method of claim 2 wherein said direct current (DC) voltage bias is varied during the step of applying said direct current (DC) voltage bias to one of said electrodes.

4. The method of claim 1 wherein the electrical potential is within the range of 0.0 and 5.0V.

5. The method of claim 1 wherein the first, second, third, and successive additional frequency vales are within the range of 10 μHz and 1 MHZ.

6. An on-line method of analyzing lubricants in real-time for thermal-oxidative breakdown, water contamination, or fuel dilution, or combinations thereof, comprising the steps of:

bringing electrodes into contact with a sample of oil;

applying a direct current (DC) voltage bias to one of said electrodes;

applying an electrical potential to the sample to produce an electrical current therethrough;

applying a sinusoidal frequency stimulus (f) to the sample to produce a frequency-dependent current response (I) therethrough;

measuring and recording a voltage response (E) from said electrical potential and sinusoidal frequency stimulus (f);

measuring and recording the frequency-dependent current response (I) during said sinusoidal frequency stimulus (f);

recording from said voltage response (E) and said frequency-dependent current response (I) the ratio of the real component (E) versus the real component (I) of said method at frequency (f);

recording from said voltage response (E) and said frequency-dependent current response (I) the ratio of the imaginary component (E) versus the imaginary component (I) of said method at frequency (f);

computing the sum of the square of said ratio of real component (E) versus real component (I) and said ratio of imaginary component (E) and imaginary component (I) all to the one-half power;

recording the magnitude of the impedance |Z| from said sum of the square of the ratio of the real component (E) versus the real component (I) and the ratio of imaginary component (E) and imaginary component (I) all to the one-half power;

recording the phase angle (θ) between said voltage response (E) and current response (I) analyzing the recorded mathematical values for said magnitude of the impedance |Z| and said phase angle (θ) to directly characterize said thermal-oxidative breakdown, water contamination, or fuel dilution conditions in said sample of oil under test;

comparing said magnitude of the impedance |Z| and phase angle (θ) values with predetermined values corresponding to said characterized sample conditions;

determining the quality and/or condition of the sample of oil as a function of the comparison; and providing an electrical indication indicative of said quality and/or condition of the sample of oil.

7. The method of claim 6, further comprising additional steps of analysis, said additional steps of analysis comprising:

a. a first analysis, wherein the applied sinusoidal frequency stimulus (f) produces a frequency-independent magnitude impedance |Z| response that increases as a function of said thermal-oxidative breakdown condition in a particular sample of oil, said first analysis thus enabling a determination of the attendant first-order reactionary pathway of the primary functional additive chemistry of the particular sample of oil;

b. a second analysis, wherein the applied sinusoidal frequency stimulus (f) produces a frequency-independent magnitude impedance |Z| response that decreases as a function of said thermal-oxidative breakdown condition in a particular sample of oil, said second analysis thus enabling a determination of the attendant first-order reactionary pathway of the primary functional additive chemistry of the particular sample of oil;

c. an analysis, wherein the applied sinusoidal frequency stimulus (f) produces a frequency-independent magnitude impedance |Z| response that increases rapidly as a function of a particular water contamination condition in the sample of oil;

d. an analysis, wherein the applied sinusoidal frequency stimulus (f) produces a phase angle (θ) response that decreases rapidly as a function of a particular water contamination condition in the sample of oil;

e. an analysis, wherein the applied sinusoidal frequency stimulus (f) produces a frequency-independent magnitude impedance |Z| response that decreases slowly as a function of a particular water contamination condition in the sample of oil;

f. an analysis, wherein the applied sinusoidal frequency stimulus (f) produces a phase angle (θ) response that decreases slowly as a function of a particular water contamination condition in the sample of oil;

g. an analysis, wherein the applied sinusoidal frequency stimulus (f) produces a frequency-independent magnitude impedance |Z| response that decreases as a function of a particular fuel contamination condition in the sample of oil; and h. an analysis, wherein the applied sinusoidal frequency stimulus (f) produces a phase angle (θ) response that increases as a function of a particular fuel contamination condition in the sample of oil.

8. The method of claim 6, wherein the step of bringing the electrodes into contact with the sample further includes bringing a temperature-sensitive resistor into thermal contact with the sample such that, from the determined oil temperature, said measurement of the magnitude of the impedance |Z| is corrected to compensate for the effects of changes in the temperature of the sample of oil.

9. The method of claim 6, further comprising recording and comparison to record the magnitude of the impedance |Z| as a direct function of the temperature of said sample of oil determined over a particular warm-up period whereby a recorded correlation with a certain temperature-viscosity relationship of said sample enables an assessment of the relative viscosity of the sample via a comparison between known viscosity conditions and said recorded correlation.

10. The method of claim 6, wherein said step of providing an electrical indication indicative of said quality and/or condition of the sample includes comparing the determined quality and/or condition of the sample with a predetermined threshold and indicating electrically if said predetermined threshold has been reached.

11. The method of claim 6, further comprising analyzing the results of said measuring steps and recording steps whereby an electrical indication is provided indicative of a remaining useful life assessment of the lubricant under test.

12. The method of claim 6, wherein said step of providing an electrical indication is enabled by a display device located in a remote position from said electrodes in contact with the sample of oil.

13. The method of claim 6, wherein said electrodes include a counter electrode and a working electrode.

14. The method of claim 6, wherein said electrodes include a counter electrode, reference electrode, and a working electrode.

15. The method of claim 6, wherein the DC voltage bias is 3.0 V or less.

16. The method of claim 6, wherein the electrical potential is within the range of 0.0 and 5.0V.

17. The method of claim 16, wherein the sinusoidal frequency stimulus (f) is less than 100 Hz.

18. The method of claim 6, wherein the sinusoidal frequency stimulus (f) is less than 1 MHZ.

19. The method of claim 18, wherein the sinusoidal frequency stimulus (f) is 1 Hz or less.

20. An in-situ, on-line system for monitoring lubricants for thermal-oxidative breakdown, water contamination, or fuel dilution, or combinations thereof, in a lubricating oil reservoir, comprising:

a. electronic power supply connected to an available 12V–72V power bus;

b. electronic instrument means connected to said power supply for generating an excitation stimulus comprised of a DC voltage bias, an electrical potential, and an alternating current (AC) drive signal, said electronic instrument means further comprising:

(i) measuring and recording means to produce a voltage response (E) from application of said excitation stimulus;

(ii) measuring and recording means to produce a frequency-dependent current response (I) from application of said excitation stimulus;

(iii) processing means for computing from said voltage response (E) and said frequency-dependent current response (I) the ratio of the real component (E) versus the real component (I);

(iv) processing means for computing from said voltage response (E) and current response (I) the ratio of the imaginary component (E) versus the imaginary component (I);

(v) processing means for computing the sum of the squares of said ratio of real component (E) versus real component (I) and said ratio of imaginary component (E) and imaginary component (I) all to the one-half power, said processing means thus enabling the determination of the magnitude of the impedance |Z|;

(vi) processing means for computing the phase angle (θ) between said voltage response (E) and said frequency-dependent current response (I);

(vii) recording means to store the mathematical values for said magnitude of the impedance |Z| and said phase angle (θ);

c. sensor means configured to be installed in an existing access port, or drain port, of the lubricating oil reservoir for applying said excitation stimulus to the lubricant contained therein, said sensor means having:
   (i) two closely-parallel, electrically-conductive electrodes extending into the lubricating oil reservoir, the two electrodes immersed in the lubricant therein and having the excitation stimulus applied thereto;
   (ii) a mechanical housing structurally supporting the physical extension of said sensor means into the lubricating oil reservoir, the mechanical housing further enabling the electrical connection, and disconnection, of said sensor means to and from said electronic instrument means for generating the excitation stimulus;
   (iii) a temperature-sensitive resistor in thermal contact with said lubricant in the lubricating oil reservoir and electrically isolated from said two electrodes, the resistor providing a voltage output for determining the temperature of said lubricant;
   (iv) an inner silicone O-ring fixtured within the inner cavity of said mechanical housing, the inner silicone O-ring providing a leak-proof seal to prevent said lubricant from contacting either the electrodes, or said temperature-sensitive resistor, within said inner cavity of the sensor means;

d. threaded housing means for fixturing said sensor means to be installed in the existing access port, or drain port, of the lubricating oil reservoir, said threaded housing means having:
   (i) a first threaded section;
   (ii) a second threaded section;
   (ii) an outer silicone O-ring fixtured immediately forward said first threaded section of the threaded housing means, the outer silicone O-ring further corresponding with the outer perimeter of said inner cavity of the sensor means and providing additional sealing to prevent the lubricant from entering either one of said sensor means or threaded housing means;
   (iii) a threaded jam nut corresponding with the mechanical housing of said sensor means to securely tighten said sensor means to said first threaded section of the threaded housing means, the tightening of said threaded jam nut thus forcing both the inner and outer O-rings into a state of compression for an even further leak-proof design;
   (iv) a third silicone O-ring fixtured immediately aft said second threaded section of the threaded housing means, the third silicone O-ring providing an additional sealing barrier between the external surface of the existing access port, or drain port, of the lubricating oil reservoir and said threaded housing means;

e. electronic potentiostat means electrically connected between the electronic instrument means and sensor means and mounted internally to said threaded housing means, said electronic potentiostat means having
   (i) a stimulus control amplifier to electronically buffer instantaneously and reproduce the excitation stimulus applied to said sensor means via said electronic instrument means;
   (ii) a voltage buffer to electronically monitor the electrical potential of said excitation stimulus and provide return electrical feedback signals to said stimulus control amplifier, said voltage buffer further transmitting the voltage response (E) as a first return voltage back to said electronic instrument means of the in-situ, on-line system;
   (iii) a current buffer to transform the resultant frequency-dependent current response (I) of said excitation stimulus into a second return voltage transmitted back to said electronic instrument means of the in-situ, on-line system;
   (iv) electronic temperature buffer means electrically connected to said temperature-sensitive resistor in thermal contact with the lubricant to current-bias the produced voltage from the temperature-sensitive resistor, said electronic temperature buffer means enabling an automatic correction of said magnitude of the impedance |Z| due to changes in the temperature of said lubricant in the lubricating oil reservoir, the electronic temperature buffer means thus providing third and fourth return voltages for the temperature-sensitive resistor and the electronic temperature buffer means respectively back to said electronic instrument means of the in-situ, on-line system;
   (v) an electrical interconnect component comprising a plurality of contacts for electrically connecting said sensor means with said electronic instrument means and the excitation stimulus therefrom, the electrical interconnect component enabling multiple cycles of engagement and disengagement of said sensor means by way of gold-over-nickel plating material;

f. electrical cable means interposed between said electronic instrument means and electronic potentiostat means, said electrical cable means conducting the excitation stimulus to the electronic potentiostat means and transmitting individually the return voltages for the voltage response (E), the transformed current response (I), the temperature-sensitive resistor, and the electronic temperature buffer means back to said electronic instrument means for further processing and analysis;

g. electronic analysis means for evaluating the processed mathematical values for said magnitude of the impedance |Z| and said phase angle (θ), said electronic analysis means enabling a direct characterization of said thermal-oxidative breakdown, water contamination, or fuel dilution conditions in the lubricant under test;

h. electronic comparison means for comparing the processed magnitude of the impedance |Z| and phase angle (θ) values with predetermined values corresponding to said characterized lubricant conditions; said electronic comparison means thus enabling a determination of the lubricant's quality and/or condition as function of the comparison; and i. electrical indication means to provide an electrical signal indicative of said quality and/or condition of the lubricant.

21. The system of claim 20, wherein the processing of said magnitude of the impedance |Z| and phase angle (θ) is done continuously to enable the simultaneous characterization of at least one of said thermal-oxidative breakdown, water contamination, or fuel dilution conditions in said lubricant under test.

22. The system of claim 20, further comprising processing and recording means to process and record the magnitude of the impedance |Z| as a direct function of said temperature of the lubricant determined over a particular warm-up period whereby a recorded correlation with a certain temperature-viscosity relationship of said lubricant enables an assessment of the relative viscosity of the lubricant via a comparison between known viscosity conditions and said recorded correlation.

23. The system of claim 20, further comprising a memory associated with said processing means for storage of analysis and/or comparison information.

24. The system of claim 20, wherein said processing means performs a trending analysis on the quality and/or condition of the lubricant.

25. The system of claim 20, wherein said electrical indication means to provide an electrical signal indicative of said quality and/or condition of the lubricant includes comparing said determined quality and/or condition of the lubricant with a predetermined threshold and indicating electrically if said predetermined threshold has been reached.

26. The system of claim 20, further comprising processing and analysis means whereby an electrical indication is provided indicative of a remaining useful life assessment of the lubricant under test.

27. The system of claim 20, wherein said electrical indication means is comprised of at least one of:
   (a) a serial communications port;
   (b) a bi-directional serial data bus chosen from among standards SAE/TMC J1708/J1587 protocol in effect on the filing date hereof, or SAE J1939 communications protocol in effect on the filing date hereof;
   (c) a CAN data bus;
   (d) a RF device; and/or
   (e) an IR device.

28. The system of claim 20, wherein said sensor means is, at the occurrence of a required lubricant change, removed from said lubricating oil reservoir and subsequently replaced.

29. The system of claim 20, further comprising processing means wherein a determination of a known high computed value for the magnitude of the impedance |Z| followed by a known lower computed magnitude impedance |Z| value is employed to determine an addition of a lubricant to said lubricating oil reservoir, said processing means and determination further enabling an automatic execution of a particular sensor calibration routine upon the detection of a fresh lubricant in contact with said electrodes.

30. The system of claim 20, further comprising processing means wherein the act of processing said real and imaginary components of the magnitude of the impedance |Z| is employed to determine said electrodes are no longer immersed in said lubricant via a computed impedance |Z| that is no longer dominantly resistive, said processing means and determination thereby enabling an indication that said lubricating oil reservoir may be void of an ample amount of said lubricant.

31. The system of claim 20, further comprising processing means wherein the act of processing said real and imaginary components of the magnitude of the impedance |Z| is employed to determine and subsequently indicate a particular cable failure via the cessation of a current response through said electrodes.

32. The system of claim 20, wherein said sensor means includes a counter electrode and a working electrode.

33. The system of claim 20, wherein said sensor means includes a counter electrode, a reference electrode, and a working electrode.

34. The system of claim 20, wherein said sensor means comprises a pair of interdigitated electrodes formed on a primary substrate component.

35. The system of claim 20, wherein the DC voltage bias is 3.0 V or less.

36. The system of claim 20, wherein the electrical potential is within the range of 0.0 V and 5.0 V.

37. The system of claim 20, wherein the alternating current (AC) drive signal is sinusoidal.

38. The system of claim 37, wherein the alternating current (AC) drive signal is less than 1 MHZ.

39. A method for sensing in-situ the electrochemical impedance characteristics of engine oil while said oil is in use in an operating combustion engine to determine the relative electrochemical condition of said oil, comprising the steps of:
   (a) placing at least two electrodes into contact with said oil;
   (b) applying a DC voltage bias to one of said electrodes;
   (c) applying an electrical potential to one of said electrodes in order to generate an electric current through said oil;
   (d) applying a sinusoidal generally constant frequency stimulus to one of said electrodes to produce a frequency-dependent response through said oil; and
   (e) measuring and recording with one of said at least two electrodes different than the first one electrode the frequency-dependent response during said step of applying the sinusoidal generally constant frequency stimulus to the impedance characteristics of said oil and thereby assess the in-situ condition of said oil as a function of an increase or decrease in said frequency-dependent response, or combinations thereof.

40. The method of claim 39, wherein the step of placing the electrodes into contact with the oil further includes bringing a temperature-sensitive resistor into thermal contact with the oil such that, from the determined oil temperature, said measurement of the frequency-dependent response is corrected to compensate for the effects of changes in the temperature of the engine oil.

* * * * *